United States Patent
Ownby et al.

(10) Patent No.: US 9,957,315 B2
(45) Date of Patent: May 1, 2018

(54) PURIFICATION OF CELL CULTURE DERIVED ALPHA1 PROTEASE INHIBITOR

(71) Applicant: Grifols, S.A., Barcelona (ES)

(72) Inventors: David Ownby, Clayton, NC (US); Thomas P. Zimmerman, Raleigh, NC (US); Jennifer A. Hunt, Raleigh, NC (US); Charles Miller, Apex, NC (US); Senthil Ranganathan, Cary, NC (US); Tonny Dessources, Raleigh, NC (US)

(73) Assignee: GRIFOLS, S.A., Barcelona (ES)

(*) Notice: Subject to any disclaimer, the term of this patent is extended or adjusted under 35 U.S.C. 154(b) by 72 days.

(21) Appl. No.: 15/138,682

(22) Filed: Apr. 26, 2016

(65) Prior Publication Data

US 2016/0304583 A1    Oct. 20, 2016

Related U.S. Application Data

(62) Division of application No. 13/828,374, filed on Mar. 14, 2013, now Pat. No. 9,353,165.

(60) Provisional application No. 61/675,560, filed on Jul. 25, 2012.

(51) Int. Cl.

| | |
|---|---|
| *C12N 7/00* | (2006.01) |
| *C12N 7/01* | (2006.01) |
| *C12N 7/02* | (2006.01) |
| *C12N 9/99* | (2006.01) |
| *C12Q 1/37* | (2006.01) |
| *A23J 1/00* | (2006.01) |
| *C07K 1/00* | (2006.01) |
| *C07K 14/00* | (2006.01) |
| *C07K 16/00* | (2006.01) |
| *C07K 17/00* | (2006.01) |
| *C07K 14/81* | (2006.01) |
| *C07K 14/47* | (2006.01) |
| *C07K 1/36* | (2006.01) |
| *C12N 15/86* | (2006.01) |

(52) U.S. Cl.
CPC ............ *C07K 14/8125* (2013.01); *C07K 1/36* (2013.01); *C07K 14/4703* (2013.01); *C12N 7/00* (2013.01); *C12N 9/99* (2013.01); *C12N 15/86* (2013.01); *C12Q 1/37* (2013.01)

(58) Field of Classification Search
CPC ................. C07K 14/8125; C07K 14/4703
See application file for complete search history.

(56) References Cited

U.S. PATENT DOCUMENTS

| | | | |
|---|---|---|---|
| 8,017,739 B2* | 9/2011 | Eichner | A61K 47/48 424/94.3 |
| 2004/0124143 A1 | 7/2004 | Kee et al. | |
| 2011/0087008 A1* | 4/2011 | Brinkman | C07K 14/775 530/359 |
| 2012/0329127 A1* | 12/2012 | Siekmann | A61K 47/4823 435/188 |

FOREIGN PATENT DOCUMENTS

| | | |
|---|---|---|
| WO | WO 02/068455 A2 | 9/2002 |
| WO | WO 2004/060528 | 7/2004 |
| WO | WO 2005/014648 A1 | 2/2005 |
| WO | WO 2007/062270 A2 | 5/2007 |
| WO | WO 2007/063299 A1 | 6/2007 |
| WO | WO 2007/112953 A1 | 10/2007 |

OTHER PUBLICATIONS

GE Healthcare Life Sciences, Capto Q; accessed Aug. 30, 2017, http://www.gelifesciences.com/webapp/wcs/stores/servletlproductById/en/GELifeSciences-us/17531602.*
Burnouf et al., Develop. Biol. Standard, 1987, 67: 31-38.*
GE Healthcare Life Sciences, Octyl Sepharose; accessed Aug. 21, 2017, http://www.gelifesciences.com/webapp/wcs/stores/servlet/productById/en/GELifeSciences-us/17094604.*
GE Healthcare Life Sciences, Capto Octyl; accessed Aug. 31, 2017, http://www.gelifesciences.com/webapp/wcs/stores/servlet/catalog/en/GELifeSciences-us/products/AlternativeProductStructure_17424/17546501.*
Carp et al., J. Clin, Invest., 66:987-95 (1980).
European search report dated Oct. 1, 2013 in corresponding EP Application No. EP13175879.9 filed Apr. 9, 2013.
Rainer Bischoff et al.; "Purification and biochemical characterization of recombinant .alpha. 1-anitryspin variants expressed in *Escherichia coli*" Biochemistry, vol. 30, No. 14, Apr. 1, 1991, ISSN:0006-2960.

* cited by examiner

*Primary Examiner* — Gary B Nickol
*Assistant Examiner* — Lakia J Jackson-Tongue
(74) *Attorney, Agent, or Firm* — Dinsmore & Shohl LLP

(57) ABSTRACT

Described herein are methods for purifying recombinant, cell culture derived $alpha_1$-protease inhibitor and removing a colored species that co-purifies with the recA1PI protein. Also described are methods for reducing the iron in cell culture derived $alpha_1$-protease inhibitor.

26 Claims, 19 Drawing Sheets

FIG. 1

(SEQ ID NO:1)

MPSSVSWGILLLAGLCCLVPVSLA EDPQGDAAQKTDTSHHDQDHPTFNKITPNLAEFAFSLYR
QLAHQSNSTNIFFSPVSIATAFAMLSLGTKADTHDEILEGLNFNLTEIPEAQIHEGFQELLRTL
NQPDSQLQLTTGNLFLSEGLKLVDKFLEDVKKLYHSEAFTVNFGDTEEAKKQINDYVEKGTQG
KIVDLVKELDRDTVFALVNYIFFKGKWERPFEVKDTEEEDFHVDQVTTVKVPMMKRLGMFNIQH
CKKLSSWVLLMKYLGNATAIFFLPDEGKLQHLENELTHDIITKFLENEDRRSASLHLPKLSITG
TYDLKSVLGQLGITKVFSNGADLSGVTEEAPLKLSKAVHKAVLTIDEKGTEAAGAMFLEAIPMS
IPPEVKFNKPFVFLMIEQNTKSPLFMGKVVNPTQK

1–24 signal peptide
E25–K418 mature peptide
N70 glycosylation
N107 glycosylation
N271 glycosylation
C256 S-nitrosylation
G368–K392 reactive center loop
F376 proteolytic cleavage site
M382–S383 reactive bond

PURIFICATION OF CELL CULTURE DERIVED ALPHA1 PROTEASE INHIBITOR

RELATED APPLICATIONS

This application is a Divisional Application of U.S. application Ser. No. 13/828,374, filed on Mar. 14, 2013, which claims priority to U.S. Provisional Application No. 61/675,560 filed on Jul. 25, 2012, the contents of each of which are incorporated by reference in their entireties herein.

TECHNICAL FIELD

Described herein are methods for purifying human recombinant cell culture derived alpha$_1$-protease inhibitor (recA1PI) and removing a colored species that co-purifies with the recA1PI protein.

BACKGROUND

Alpha$_1$-proteinase inhibitor (abbreviated herein as A1PI; also known as alpha-1 protease inhibitor, alpha-1 PI, A$_1$PI, α-1 PI, α$_1$PI, alpha-1 trypsin inhibitor, alpha$_1$ antitrypsin, alpha-1 antitrypsin, alpha1AT, A1A, and A1AT, AAT, inter alia), is the major serine protease inhibitor (serpin) in humans. A1PI is expressed as a 418 amino acid protein with residues 1-24 being a signal peptide. The mature protein, consisting of residues 25-418, is a single chain glycoprotein having a molecular weight of about 51 kD. See FIG. 1. While A1PI does not contain any disulfide bonds, the protein is highly structured, with 80% of the amino acids residing in eight well-defined α-helices and three large β-sheets. Three asparagine-linked carbohydrates are found on Asn 70, Asn 107, and Asn 271 (numbered as in the full-length protein). This gives rise to multiple A1PI isoforms, having isoelectric points in the range of 4.0 to 5.0. The glycan monosaccharides include N-acetylglucosamine, mannose, galactose, fucose, and sialic acid.

Normal plasma concentrations of A1PI range from 1.3 to 3.5 mg/mL. A1PI functions by protecting cells from proteases involved in clotting and inflammation. A1PI inhibits trypsin, chymotrypsin, various forms of elastases, skin collagenase, renin, urokinase, and proteases of polymorphonuclear lymphocytes, among others. A1PI serves as a pseudo-substrate for these proteases, which attack the reactive center loop of the A1PI molecule (residues Gly 368-Lys 392) by cleaving the bond between residues Met 358-Ser 359 forming an A1PI-protease complex. This complex is rapidly removed from the blood circulation. One of the endogenous roles of A1PI is to regulate the activity of neutrophil elastase, which breaks down foreign proteins and injures native tissue present in the lung. In the absence of sufficient quantities of A1PI, the elastase breaks down lung tissue, which over time results in chronic lung tissue damage and emphysema.

A1PI is often purified from blood plasma. See, e.g., U.S. Pat. Nos. 6,284,874; 6,462,180; 6,093,804; 7,879,800; and WO 1998/000154; WO 2002/048176; WO 2010/009388, for example. In addition, recombinant A1PI (recA1PI) can be expressed and purified from a variety of sources. See, e.g., U.S. Pat. Nos. 4,931,373 and 5,134,119; U.S. Patent Application Publications Nos. US 2004/0124143 and US 2007/0218535; PCT Publication Nos. WO 2005/047323 and WO 2010/127939; and Archibald et al., *Proc. Natl. Acad. Sci. USA* 87:5178-5182 (1990); Wright et al., *Nat. Biotechnology* 9: 830 (1991).

Methods for expressing and purifying human recombinant, cell culture derived A1PI for therapeutic use are described herein. Following purification, the A1PI solution had a yellow or amber color that may be objectionable to clinicians and/or patients. Methods for diminishing the coloration are also described herein.

SUMMARY

One embodiment described herein is a method of diminishing an amount of colorant in a solution comprising cell culture derived alpha$_1$ proteinase inhibitor (recA1PI) comprising incubating the solution comprising recA1PI with a reducing agent and separating the recA1PI from the colorant.

In some aspects described herein, the reducing agent is cysteine or DTT.

In some aspects described herein, the reducing agent is cysteine.

In some aspects described herein, the reducing agent concentration is from about 1 mM to about 100 mM.

In some aspects described herein, the reducing agent concentration is about 10 mM.

In some aspects described herein, the reducing agent concentration is about 1 mM.

In some aspects described herein, the reducing incubation step is carried out for a time of from about 1 to about 24 hours.

In some aspects described herein, the reducing incubation step is carried out at a temperature of from about 2° C. to about 60° C.

In some aspects described herein, the reducing agent is 10 mM cysteine and the incubation is carried out overnight at about room temperature.

In some aspects described herein, the separating the recA1PI from the colorant comprises chromatography.

In some aspects described herein, the chromatography comprises ion exchange, hydrophobic interaction, gel filtration, affinity, immunoaffinity, or combinations thereof.

In some aspects described herein, the method comprises reducing the iron concentration.

In some aspects described herein, the iron concentration is reduced (i.e., lowered) 2-to 100-fold.

In some aspects described herein, the iron concentration is reduced (i.e., lowered) 5-to 50-fold.

In some aspects described herein, the iron concentration is 10 µM or less.

In some aspects described herein, the iron concentration is 1 µM or less.

Another embodiment described herein is a method of purifying cell culture derived human A1PI from an aqueous solution comprising recA1PI, comprising: (a) performing a viral inactivation step on a solution containing recA1PI; (b) passing the virally inactivated solution through an anion exchanger so that recA1PI binds to the anion exchanger; (c) eluting recA1PI from the anion exchange resin to obtain an anion exchange eluate containing recA1PI; (d) adding a reducing agent to the anion exchange eluate containing recA1PI to obtain a reducing solution; (e) incubating the reducing solution; (f) passing the reducing solution through a hydrophobic interaction chromatography (HIC) resin so that recA1PI binds to the HIC resin; and (g) eluting recA1PI from the HIC resin to obtain an HIC eluate that contains recA1PI.

In some aspects described herein, the viral inactivation comprises a solvent/detergent incubation.

In some aspects described herein, the solvent is added in a range of 0.01% to about 0.5%.

In some aspects described herein, the detergent is added from about 0.5% to about 2.0% weight per volume of the resulting mixture.

In some aspects described herein, the solvent/detergent incubation comprises adding about 0.5% polysorbate 20 and about 0.03% tri(n-butyl phosphate) at pH of about 8 and a temperature of about 30° C.

In some aspects described herein, the anion exchanger is a quaternary ammonium resin.

In some aspects described herein, the quaternary ammonium resin is Capto™ Q.

In some aspects described herein, the reducing agent is cysteine (Cys); cysteamine; dithiothreitol (DTT); dithioerythritol (DTE); glutathione (GSH); 2-mercaptoethanol (2-ME); 2-mercaptoethylamine (2-MEA); tris(2-carboxyethyl)phosphine (TCEP); oxalic acid; formic acid; ascorbic acid; nicotinamide adenine dinucleotide (NADH); nicotinamide adenine dinucleotide phosphate (NADPH); or combinations thereof.

In some aspects described herein, the reducing agent is cysteine or DTT.

In some aspects described herein, the reducing agent is cysteine.

In some aspects described herein the reducing agent concentration is from about 1 mM to 100 mM.

In some aspects described herein, the reducing agent concentration is about 10 mM.

In some aspects described herein, the reducing agent concentration is about 1 mM.

In some aspects described herein, the reducing incubation step is carried out for about 1 to 24 hours.

In some aspects described herein, the reducing incubation step is carried out from about 2° C. to 60° C.

In some aspects described herein, the reducing agent is 10 mM cysteine and the incubation is carried out overnight at about room temperature.

In some aspects described herein, the HIC resin is Octyl Sepharose™ or Capto™ Octyl.

In some aspects described herein, the method comprises reducing the iron concentration.

In some aspects described herein, the iron concentration is reduced (i.e., lowered) 2-to 100-fold.

In some aspects described herein, the iron concentration is reduced (i.e., lowered) 5-to 50-fold.

In some aspects described herein, the iron concentration is 10 µM or less.

In some aspects described herein, the iron concentration is 1 µM or less.

Another embodiment described herein is a method of purifying cell culture derived alpha$_1$ proteinase inhibitor (recA1PI) comprising incubating a solution comprising recA1PI with a reducing agent and separating the recA1PI from the reducing agent and the reduced species.

In some aspects described herein, the reducing agent is cysteine or DTT.

In some aspects described herein, the reducing agent is cysteine.

In some aspects described herein, the reducing agent concentration is from about 1 mM to about 100 mM.

In some aspects described herein, the reducing agent concentration is about 10 mM.

In some aspects described herein, the reducing agent concentration is about 1 mM.

In some aspects described herein, the incubation step is carried out for a time of from about 1 to about 24 hours.

In some aspects described herein, the incubation step is carried out at a temperature of from about 2° C. to about 60° C.

In some aspects described herein, the reducing agent is about 10 mM cysteine and the incubation is carried out overnight at about room temperature.

In some aspects described herein, the separating the recA1PI from the reducing agent and reduced species comprises chromatography.

In some aspects described herein, the chromatography comprises ion exchange, hydrophobic interaction, gel filtration, affinity, immunoaffinity, or combinations thereof.

In some aspects described herein, the reduced species comprises iron.

In some aspects described herein, the iron concentration is reduced (i.e., lowered) 2-to 100-fold.

In some aspects described herein, the iron concentration is reduced (i.e., lowered) 5-to 50-fold.

In some aspects described herein, the iron concentration is 10 µM or less.

In some aspects described herein, the iron concentration is 1 µM or less.

BRIEF DESCRIPTION OF THE DRAWINGS

FIG. 1 illustrates the primary sequence (SEQ ID NO: 1) of human A1PI and notable modification sites.

DETAILED DESCRIPTION

Figure 2:
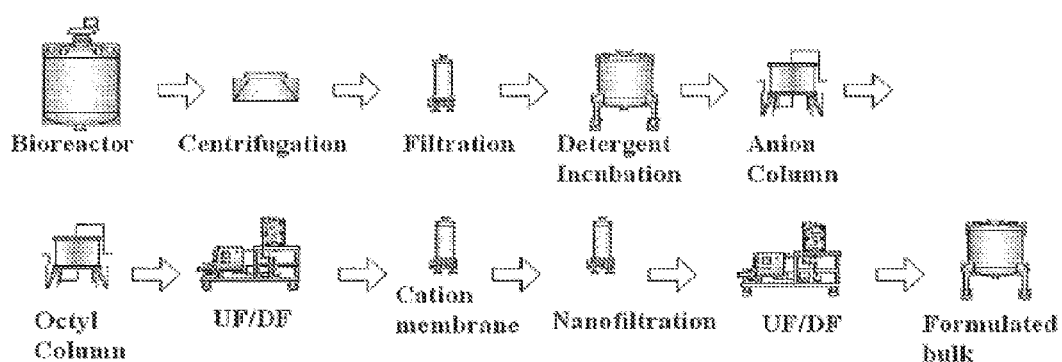
FIG. 2 shows a flow chart of the purification process used for purifying recA1PI that results in a purified recA1PI solution having a yellow color.

Described herein are methods for purifying recombinant, cell culture derived alpha$_1$-protease inhibitor and removing a colored species that co-purifies with the recA1PI protein.

One aspect described herein is a method of purifying recombinant, cell culture derived human A1PI from an aqueous solution containing recA1PI.

Another method described herein is a method of diminishing the coloration of a solution of recombinant, cell culture derived A1PI comprising incubating the recA1PI solution with a reducing agent and separating the recA1PI from reducing agent and the colored species.

Another method described herein is a method of purifying recombinant, cell culture derived A1PI comprising incubating a recA1PI solution with a reducing agent and separating the recA1PI from the reducing agent and the reduced species.

EXAMPLES

Example 1

Cell Growth and Expression of Human Recombinant A1PI

Summary

The expression of recombinant human A1PI begins by culturing human PER.C6® cells (Crucell, Leiden, Netherlands) containing a pAATopST3 plasmid construct for expressing glycosylated human recA1PI. These cells are capable of producing high yields of glycosylated recA1PI, i.e., up to 22 picograms recA1PI per cell per day (pcd). The PER.C6®/recA1PI culture was taken through a series of scale-up steps through a 10 L wave bioreactor and a 200 L bioreactor with a target working volume of 150 L. The culture supernatant containing the recA1PI was harvested 13-14 days later by centrifugation at 6,000 rpm in a Celeros Centrifuge (Celeros Separations, Foxboro, Mass.) followed by filtration prior to purification.

Vial Thaw and Shake Flask Inoculum Train

The cell culture process began with the thawing of a cryovial of PER.C6® (Crucell) human cells containing a pAATopST3 plasmid construct for expressing glycosylated human recA1PI. Descriptions of the human recombinant alpha$_1$ protease inhibitor clone, expression, and analyses of the expressed recombinant A1PI are described in WO 2010/127939 and U.S. patent application Ser. No. 13/138,912, which are incorporated by reference herein for such teachings. After the vial of cells was thawed, the cells were transferred to a 125-mL flat-bottom shake flask and brought to a final volume of 15-25 mL of CDM4PERMAb™ basal media (Hyclone) for a target viable cell density of $0.5 \times 10^6 \pm 0.1 \times 10^6$ cells/mL. The 125 mL shake flask (Passage #1) were incubated for 96±4 hours at 90 rpm, 36.5° C., 5.0% $CO_2$. The cells were then transferred to a 250 mL flat-bottom shake flask with a target volume of 100 mL and a viable cell density of $0.5 \times 10^6 \pm 0.1 \times 10^6$ cells/mL. The 250 mL flat-bottom shake flask (Passage #2) was incubated for 72 to 96 hours (±4 hours) at 125 rpm, 36.5° C., 5.0% $CO_2$. The cells were then transferred to a 500-mL flat-bottom shake flask with a target volume of 250 mL and a viable cell density of $0.5 \times 10^6 \pm 0.1 \times 10^6$ cells/mL. The 500 mL flat-bottom shake flask (Passage #3) was incubated for 72 to 96 hours (±4 hours) at 125 rpm, 36.5° C., 5.0% $CO_2$. The cells were then transferred to a 1 L flat-bottom shake flask with a target volume of 600 mL and a viable cell density of $0.5 \times 10^6 \pm 0.1 \times 10^6$ cells/mL. The 1 L flat-bottom shake flask (Passage #4) was incubated for 72 to 96 hours (±4 hours) at 125 rpm, 36.5° C., 5.0% $CO_2$.

Wave Bioreactor Inoculum Train

The volume from the 1 L shake flask was transferred to a 10 L Cellbag® on a 20/50EH Wave™ Bioreactor (GE Healthcare Life Sciences) to achieve a working volume of 3.0-4.0 L and a viable cell density of $0.5 \times 10^6 \pm 0.1 \times 10^6$ cells/mL. The 10 L Cellbag® was operated for 72 to 96 hours (±4 hours) at 25 rpm, 7°-rocking angle, 0.2 liters per minute (lpm) air flow rate, 36.5° C., and 3.0% $CO_2$. The volume from the 10 L Cellbag was transferred to a 50 L Cellbag® on a 20/50EH Wave Bioreactor to achieve a working volume of 22-25 L and a viable cell density of $0.5 \times 10^6 \pm 0.1 \times 10^6$ cells/mL. The 50 L Cellbag® was operated for 72 to 96 hours (±4 hours) at 22 rpm, 7° rocking angle, 0.3 lpm air flow rate, 36.5° C., and 3.0% $CO_2$.

200 L Bioreactor

The contents of the 50 L Cellbag® were transferred to the Xcellerex 200 L bioreactor through a sterile Kleenpak™ connection (Xcellerex, Marlborough, Mass.). The 200 L bioreactor should contain a minimum amount (100 L) of CDM4PERMAb™ basal media (Hyclone) and be operational at 36.5° C., 120 rpm, with a pH in the range of 7.2±0.4 prior to the addition of inoculum. The target working volume was 150 L at a viable cell density of $0.6 \times 10^6$ cells/mL±$0.1 \times 10^6$ cells/mL. The pH dead band (an area of signal range where no action occurs) was 7.2±0.4 and the dissolved oxygen setpoint was 50%. The pH was maintained by addition of 1 N sodium carbonate or $CO_2$ gas. At 96 hours (±4 hours), PerMAB™ feed media (Hyclone) was added as a daily bolus shot equal to 0.3% of the initial working volume in the bioreactor; the feed media was added at a flow rate of 100-300 mL/min. The feed media was maintained at room temperature during the run and was covered to prevent any degradation by light. Antifoam was added at the start of the run at 12 ppm and was added in small increments to maintain a foam level in the bioreactor that was 2 inches or less. The 200 L bioreactor was harvested at 308-340 hours (12.8-14.2 days).

Centrifugation and Filtration

The material from the 200 L bioreactor was transferred to the Celeros APD-75 1 L bowl at a flow rate of 0.5 lpm with centrifugation speed of 6,000 rpm (Celeros Separations, Foxboro, Mass.). The percent solids value was calculated prior to transfer to determine the number of bowl discharges needed (the 1 L bowl can hold 1 kg of solids). The centrate (the clarified solution following centrifugation) was transferred to a Millipore Pilot POD holder that contains two 1.1 m² A1HC filters at 1 lpm (EMD Millipore, Billerica, Mass.). Post depth-filtration, the material was filtered through a 0.5/0.2 µm Millipore SHC filter.

Example 2

Purification of Human Recombinant A1PI from Cell Culture Supernatant

Summary

The purification of recA1PI begins with a three-hour solvent/detergent treatment for viral inactivation. The recA1PI was then captured and eluted from a Capto™ Q column (GE Healthcare Life Science, Piscataway, N.J.). The following day, the purification was continued on an Octyl Sepharose™ column. The HIC eluate was ultrafiltered and diafiltered to enable S-membrane purification that was followed by nanofiltration for additional viral clearance. This material was buffer-exchanged into the final formulation buffer and the protein concentration was adjusted to make the formulated bulk.

Viral Inactivation of Cell Culture Supernatant

The depth-filtered cell culture supernatant was weighed, the $A_{280}$ read, and aliquots taken for sampling. The temperature and pH set points for this viral inactivation step were 28° C.±2° C. and a pH of 7.8±0.2. A 100-× stock of the TNBP/polysorbate 20 was used for the treatment, prepared by mixing 0.5 kg of polysorbate 20, 0.06 kg of tri-(n-butyl) phosphate (TNBP), and water for injection (WFI) to make up a liter of the mixture. This stock was added to the cell culture supernatant at a 100-fold dilution and the treatment carried out for 2.5 hours with stirring. The final concentrations were 0.5% for the polysorbate 20 and 0.03% for the TNBP. Following the TNBP/polysorbate 20 treatment, the cell culture supernatant was filtered.

Filtration

A Cuno 120ZA Filter Disc (3M, St. Paul, Minn.) was rinsed with hot water for injection (HWFI) at not more than 1 L/min for at least 10-minutes. This was followed by a rinse with cold water for injection (CWFI) of not less than 2 L and finally air dried at 20 psi. The TNBP/polysorbate 20-treated cell culture supernatant was passed through this filter using an air pressure not less than 20 psi and a flow, no greater than 1 L/minute. Aliquots were taken for sampling and retains.

Anion Exchange Chromatography

This step serves to capture recA1PI and eliminate host cell proteins (HCPs) in the flow-through. A 30 cm inner diameter×14 cm bed height column was used (10 L bed volume). The pH of the TNBP/polysorbate 20-treated cell culture supernatant was adjusted back to 7.0±0.1. The conductivity of the solvent/detergent-treated supernatant prior to column loading was measured. The amount of ambient WFI diluent was determined to ensure that the conductivity was no higher than 4 mS/cm during column loading with inline dilution.

The Unicorn program (GE Healthcare Life Sciences) was used to run the Capto™ Q column (GE Healthcare Life Science) and the inlet lines of the chromatography system were placed in the appropriate buffer tanks. A Durapore 0.3 µm in-line filter (Millipore) was changed for every chromatography run. The Capto™ Q column was pre-equilibrated with 1 column volume (CV) of 0.5 M glacial acetic acid followed by equilibration with 5 CVs of 20 mM $Na_2HPO_4$, pH 6.0. The cell culture supernatant was loaded onto the Capto™ Q column by in-line dilution with water for injection (WGI). The chromatography skid was programmed to perform the loading at a conductivity not more than 4 mS/cm at a linear flow rate of 300 cm/h. The loading was followed by a brief chase with WFI. The column was washed with 8 CV of wash buffer (20 mM $Na_2HPO_4$, 20 mM NaCl pH 6.0) prior to a 2 CV re-equilibration with 20 mM $Na_2HPO_4$, pH 6.0. Elution was accomplished using an 8 CV gradient ending in 25 mM $Na_2HPO_4$, 200 mM NaCl, pH 7.0 or by a step-wise increase in NaCl concentration. The single elution peak of recA1PI was collected beginning at 4 CV into the gradient and collection ends with a UV-watch gate of 0.10 AU. The elution fraction was sampled for testing and retained. L-cysteine was added to the eluate pool at a concentration of 10 mM and allowed to mix overnight at room temperature.

Hydrophobic Interaction Chromatography using Octyl Sepharose™ FF

A 45 cm inner diameter×9 cm bed height column (15 L bed volume) Octyl Sepharose™ 4 FF hydrophobic interaction chromatography (HIC) column (GE Healthcare Life Sciences) was equilibrated with 8 CV of HIC equilibration buffer (25 mM $Na_2HPO_4$, 0.1 M NaCl, 1.75 M ammonium sulfate, pH 7.0). The Capto Q eluate containing A1PI and cysteine was loaded by inline dilution with the octyl dilution buffer (25 mM $Na_2HPO_4$, 0.1 M NaCl, 3 M $(NH_4)_2SO_4$, pH 7.0) at a flow rate of 150 cm/h to achieve a final concentration of 1.75 M $(NH_4)_2SO_4$ in the loading material. Following loading, the column was washed with 5 CV of the HIC equilibration buffer. Elution was accomplished with a reverse salt gradient from the 1.75 M ammonium sulfate in the wash buffer to the elution buffer (20 mM $Na_2HPO_4$, pH 6.0) over 10 CV. UV absorbance watch commands of 0.05 AU on the front and 0.10 AU on the tail were used to collect the eluate pool.

Ultrafiltration and Diafiltration of the HIC Eluate

Three 30 kDa molecular weight cut off (MWCO) 0.1 m² membranes were flushed with WFI at 40-50° C. until the pH of the permeate and retentate were between 5 and 7. The feed pressure was set to a target of 25 (e.g., a range of 24 to 28) psig while the outlet pressure was set to 5 psig (e.g., a range of 4 to 8 psig). The system was equilibrated with 1-2 L of the HIC elution buffer for not less than 10 minutes. The HIC eluate was mixed and the temperature maintained at 15-25° C. The permeate volume was monitored and, the UF was stopped when the concentration has reached an $A_{280}$ target of 30. Following the reduction in the volume of the feed, diafiltration was performed with 6 diavolumes (DV) of the cation equilibration buffer (10 mM sodium citrate, pH 5.4). The $A_{280}$ of the retentate was checked to ensure that it was ≤30 and the retentate was drained into a clean vessel. Two 1-L volumes of cation equilibration buffer were each recirculated with a feed pressure of 10-15 psig for not less than 5 minutes. The rinses were combined with the retentate.

Cation Exchange Chromatography using an S Membrane

A Sartobind® S-membrane single use capsule (Sartorius, Gottingen, Germany) with a membrane surface area of 2500 cm² was equilibrated with the cation equilibration buffer (10 mM sodium citrate dihydrate, pH 5.4) ensuring that the conductivity of the effluent was not more than 4 mS/cm. The UF/DF-treated HIC eluate was loaded onto the S-membrane at 25 L/h using a peristaltic pump and subsequently washed with cation equilibration buffer until the $A_{280}$ was not more than 0.1 AU. The flow-through was collected and adjusted to pH 7.0±0.1.

Nanofiltration

Nanofiltration was performed using a Viresolve® NFP (0.085 m²; Millipore) with the Viresolve® PreFilter (0.11 m²). Filtration was by constant pressure with a pressure can at not more than 50 psi. The nanofilter was rinsed with four 500 mL volumes of cation equilibration buffer.

Final Ultrafiltration/Diafiltration

A 10 kDa MWCO membrane with a 0.3 m² membrane area was used in this step. The holder and membrane were flushed with WFI at 40-50° C. until the pH of the permeate and retentate was between 5 and 7. The feed pressure was set to a target of 25 psig (range of 24 to 28 psi) while the outlet pressure was set to 5 psig (range of 4 to 8 psi). The system was equilibrated with 1-2 L of 20 mM $Na_2HPO_4$, pH 7.0 for not less than 10 minutes. The nanofiltrate was mixed well and the temperature maintained at 15-25° C. The permeate was checked periodically for loss of recA1PI by measuring its absorbance at 280 nm (i.e., $A_{280}$) which should be <0.04. If this value was exceeded, the UF/DF was stopped. The permeate volume was monitored and the UF was stopped when the concentration has reached an $A_{280}$ target of ~30. Following the reduction in the volume of the feed, diafiltration was performed with 5 DV of the diafiltration buffer (20 mM $Na_2HPO_4$, 120 mM NaCl, pH 7.0). The $A_{280}$ of the retentate was checked to ensure that it was ≤30 and the retentate was drained into a clean vessel. The amount of diafiltration buffer rinse was calculated which, when added to the retentate, will result in a final concentration of 50-56 mg/mL. This rinse volume was divided in half and each volume was recirculated with a feed pressure of not more than 20 psig for 3-5 minutes. The rinses were combined with the retentate.

Storage

The concentrated bulk recombinant A1PI was sterile filtered into Flexel® bags (Sartorius) and stored at −70° C., prior to final filling.

The recA1PI produced by the method described above was found to have a marked yellow color. The identity of the yellow species was unknown. Although the recA1PI was highly pure and active, removal of the yellow colorant was desired for aesthetic reasons.

Example 3

Immunoaffinity Chromatography with Alpha-1 Antitrypsin Select Resin

Figure 3:
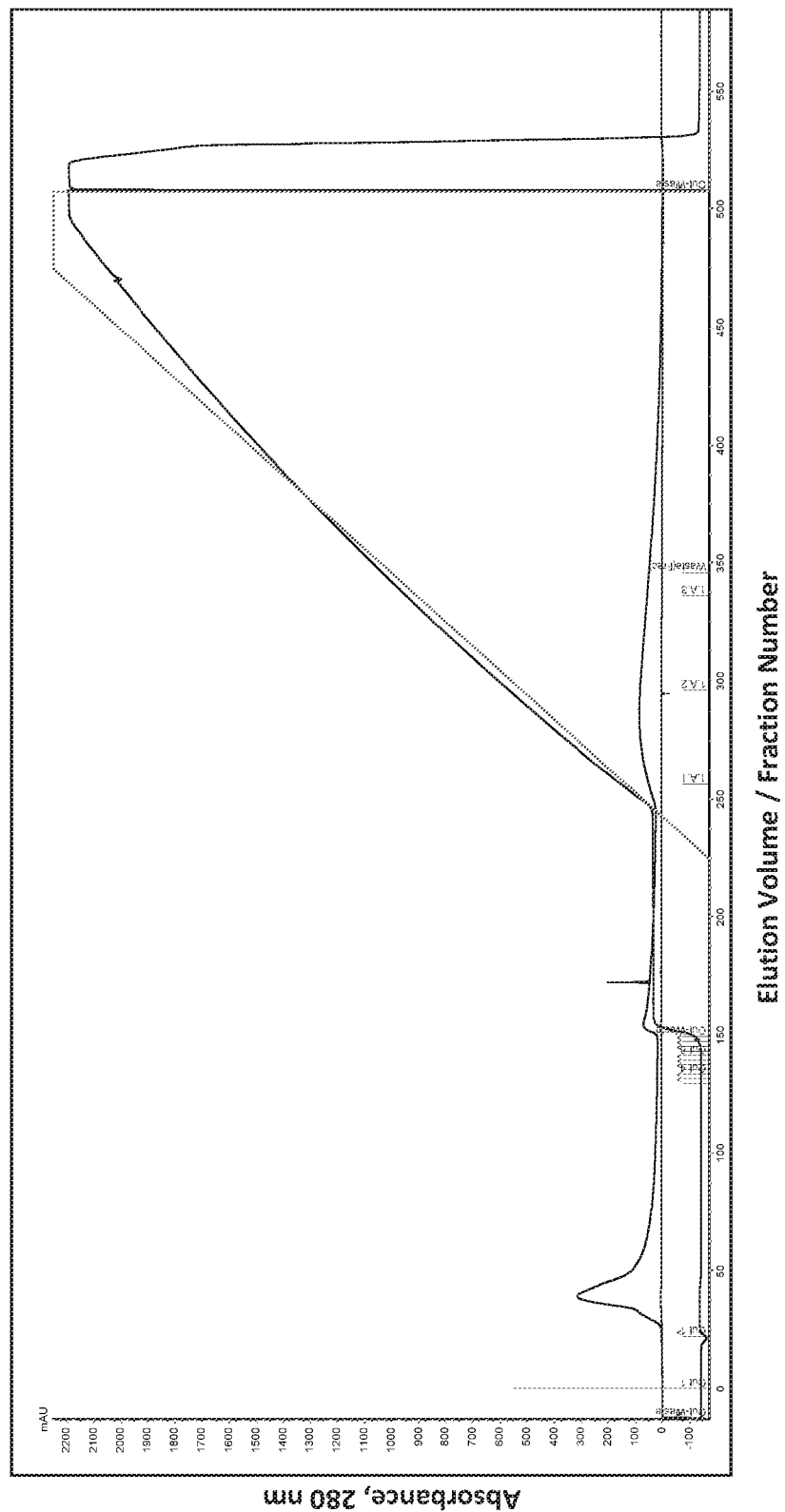
FIG. 3 shows a chromatogram of a sample of recA1PI purified by immunoaffinity chromatography (i.e., ATT Select resin, GE Healthcare Life Sciences).

An A1PI-specific immunoaffinity column was performed to determine whether the yellow species could be separated from the purified recA1PI. A 1.6 cm inner diameter×10 cm bed height column (20 mL column volume) of Alpha-1 Antitrypsin Select resin (AAT-Select; GE Healthcare Life Science), specific for the plasma-derived H1PI was packed. The column was equilibrated with 20 mM Tris.HCl, pH 7.4. Approximately 200 mg of recA1PI at 10 mg/mL was loaded onto this column at 5 mL/minute. The column was washed with 20 mM Tris.HCl, pH 7.4, 100 mM NaCl and eluted with 20 mM Tris.HCl, pH 7.4, 2 M NaCl (see FIG. 3). Fractions were collected based on peak fractionation. The fractions under the elution peak were pooled and concentrated using Amicon UltraCel™ 30 kDa MWCO concentrators (EMD Millipore, Billerica, Mass.). A UV-Vis spectrum was acquired from the concentrated sample.

Figure 4:
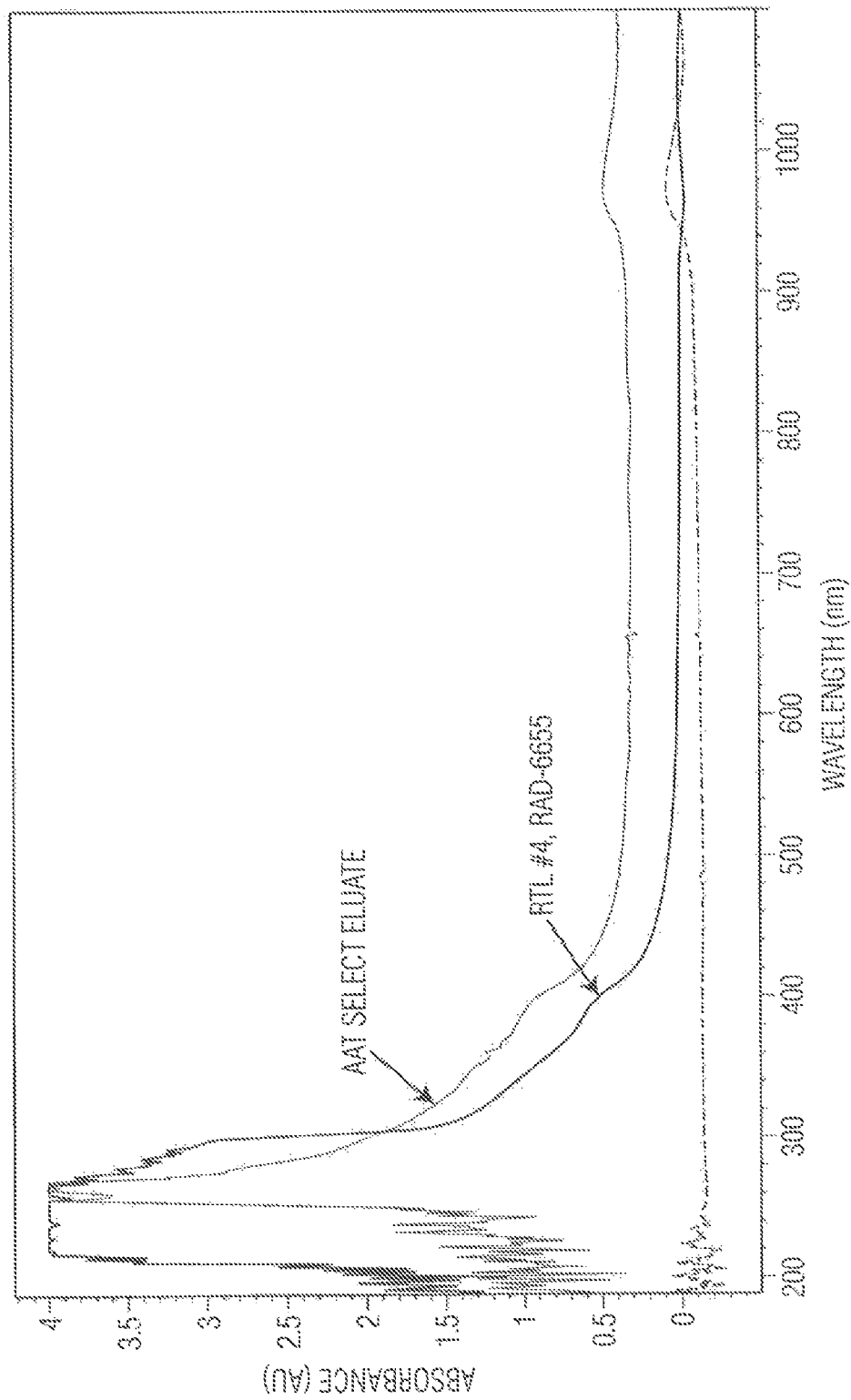
FIG. 4 shows a UV-Vis spectrum of a sample of recA1PI purified by immunoaffinity chromatography (i.e., ATT Select resin, GE Healthcare Life Sciences).

The eluate, following concentration, was distinctly yellow in color. When analyzed by UV-Vis spectroscopy (see FIG. 4), the spectrum was very similar to that seen for recA1PI prior to running the immunoaffinity column. The conclusion from this result was that immuno-affinity chromatography was ineffective at separating the yellow color from recA1PI.

Example 4

Gel Filtration Chromatography with Superdex™ 200 Resin

A gel filtration experiment (aka size exclusion chromatography; SEC) was also attempted to remove the yellow species from recA1PI. A 1.6 cm inner diameter×90 cm column (bed volume of 181 mL) of Superdex™ 200 prep grade resin was packed (GE Healthcare Life Sciences). The column was equilibrated with phosphate buffered saline (PBS; 12 mM phosphates, pH 7.4, 137 mM NaCl, 2.7 mM KCl). recA1PI was loaded at 5% of the column volume (9 mL) and run at 2 mL/minute (60 cm/h). Fractions of 12 mL volume were collected for analysis.

Figure 5:
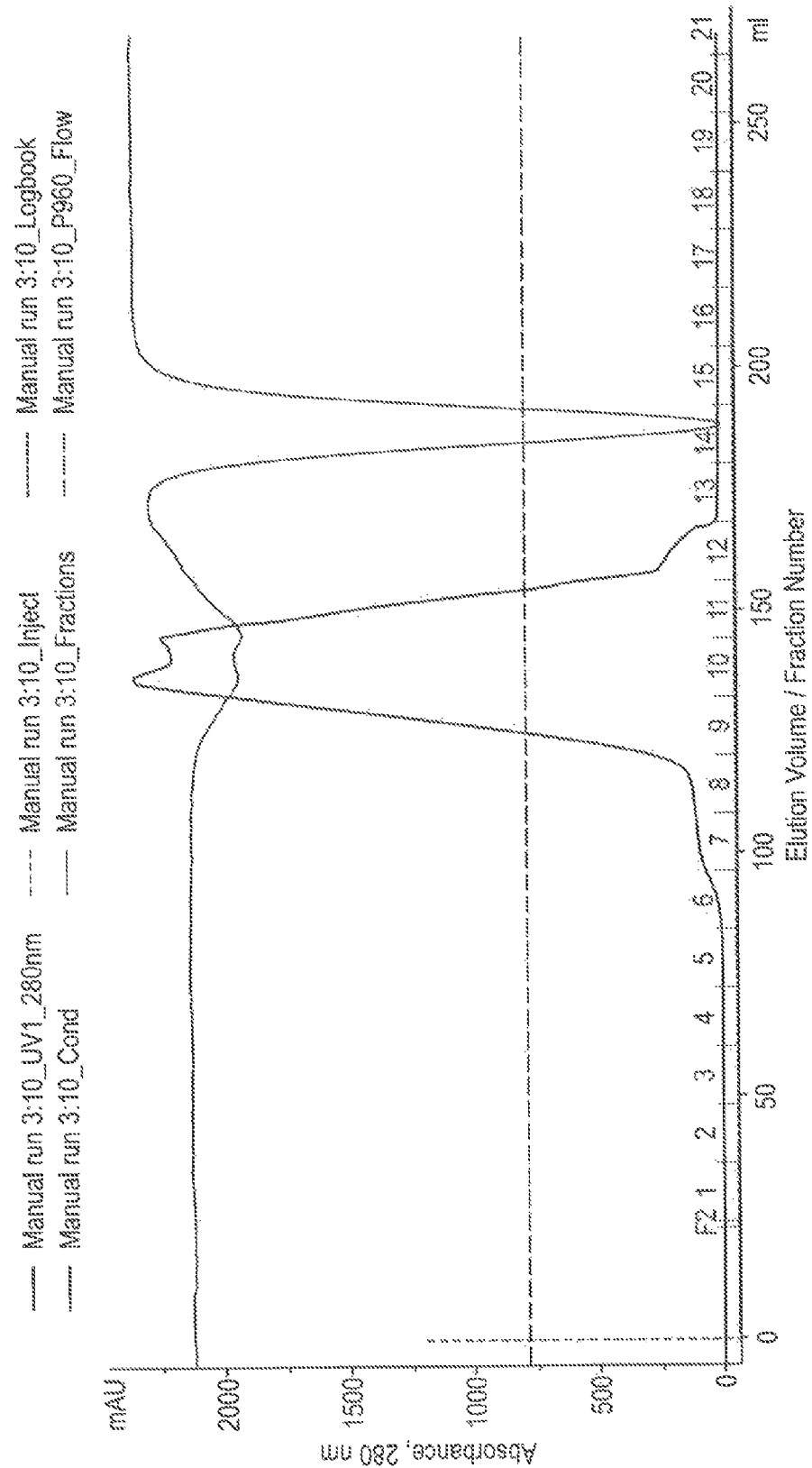
FIG. 5 shows a chromatogram of a sample of recA1PI purified by gel filtration (i.e., size exclusion) chromatography using Superdex™ 200 prep grade resin (GE Healthcare Life Sciences).
Figure 6:
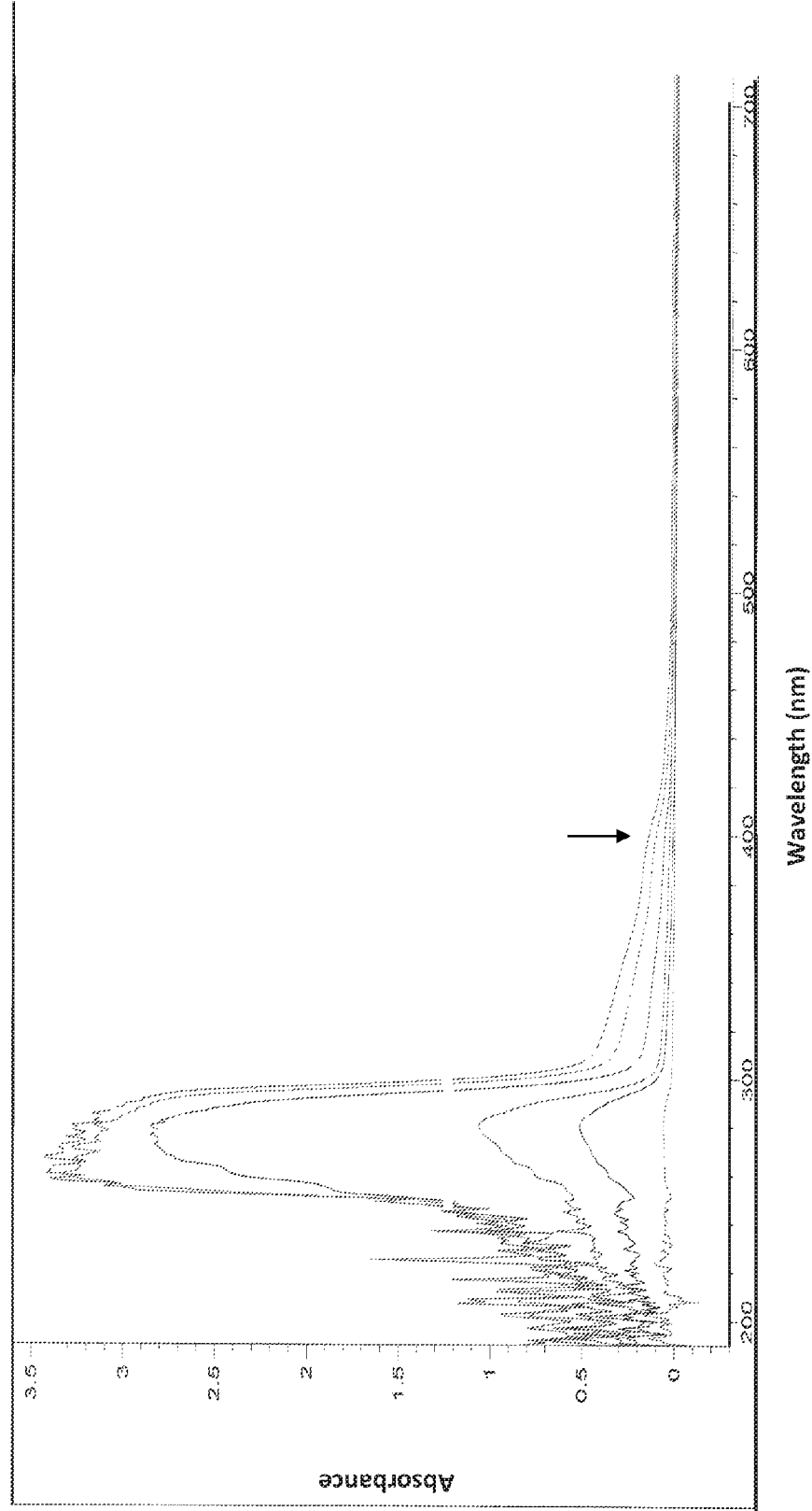
FIG. 6 shows a UV-Vis spectrum of a sample of recA1PI purified by gel filtration (i.e., size exclusion) chromatography using Superdex™ 200 prep grade resin (GE Healthcare Life Sciences).

The chromatogram for this column is shown in FIG. 5. Although, the load is 99% recA1PI, a split peak was observed, possibly owing to saturation of the UV detector. The fractions under this peak were analyzed by UV-Vis spectrophotometry (FIG. 6). The recA1P fractions were visibly yellow and the UV-Vis spectra of these fractions were similar to that of the loading material. Accordingly, the gel filtration column did not remove the yellow color from recA1PI.

Example 5

Denaturant and Reducing Agent Analyses

Because immunoaffinity and gel filtration chromatography were not successful in removing the yellow color from recA1PI the use of denaturants and/or reducing agents were sought as potential means for removing or diminishing the yellow color.

Approximately 1 mL of the recA1PI was mixed with 8 M guanidine hydrochloride or 500 mM DTT to achieve final concentrations of 4 M guanidine hydrochloride or 50 mM DTT, respectively. A third sample was mixed with both reagents. The samples were incubated at 50° C. for approximately 2 h and individually passed through PD-10 desalting columns (GE Healthcare Life Sciences). The flow-through from these columns was collected by centrifugation at 1,000×g for 5 minutes.

Figure 7:
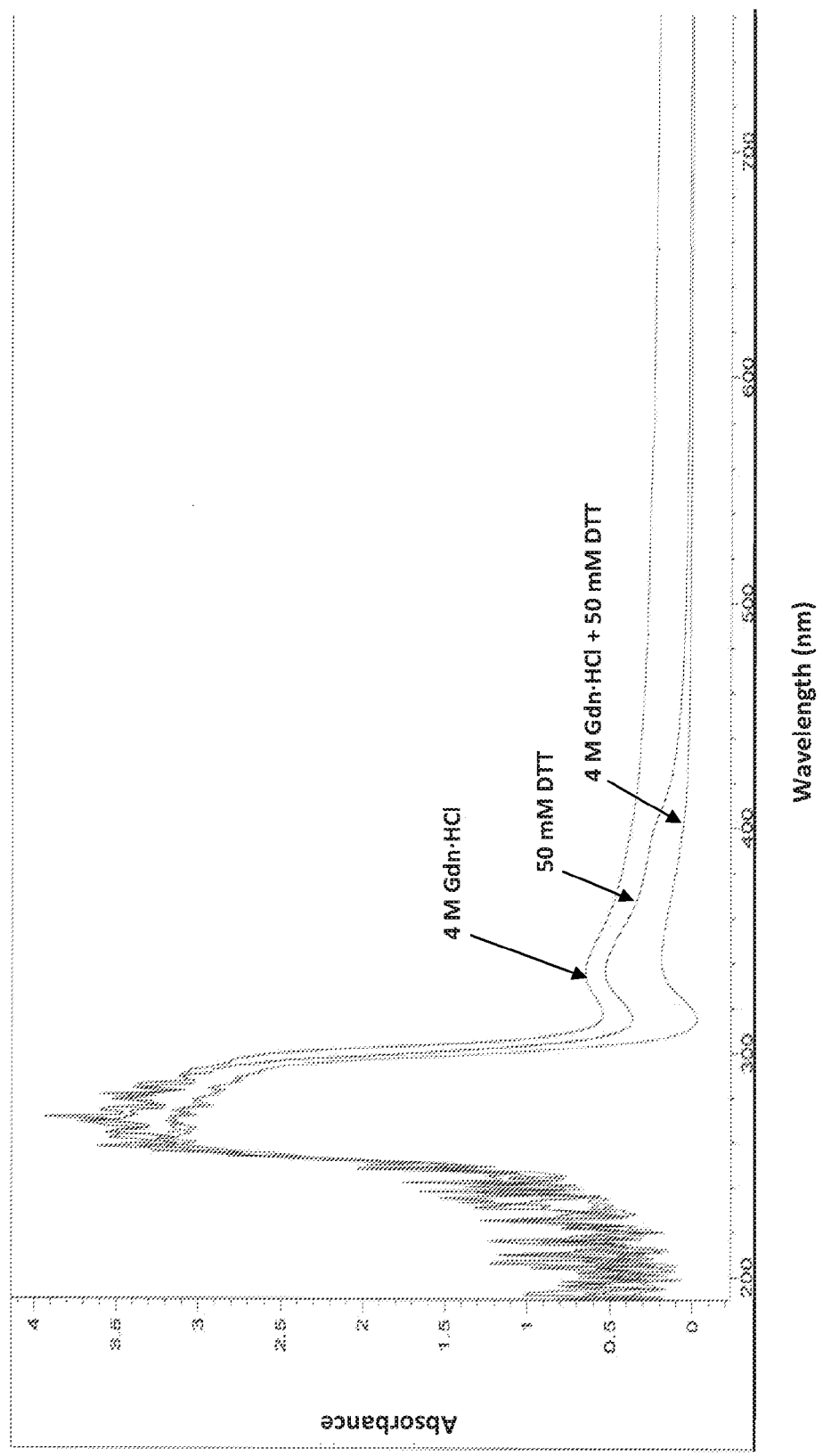
FIG. 7 shows UV-Vis spectra of three samples of human recombinant, cell culture derived A1PI having a yellow color. Sample 1 contains 4 M guanidine hydrochloride (Gdn.HCl); sample 2 contains 50 mM dithiothreitol (DTT); sample 3 contains both 4 M Gdn.HCl and 50 mM DTT.

Guanidine hydrochloride did not help with diminution and this was reflected in the UV-Vis spectrum of this sample (FIG. 7). The 50 mM DTT treated sample was lighter yellow compared with the guanidine hydrochloride treated sample. This sample did not have the spectral signature at 405 nm that was characteristically observed for the recA1PI (FIG. 7). The sample treated with the combination of guanidine and DTT was nearly colorless and missing in the spectral features in the 300-400 nm range. The fact that both the guanidine hydrochloride and the DTT were required to diminish the yellow color may indicate that the yellow colored species is covalently bound to recA1PI.

Example 6

Reduction and Gel Filtration Chromatography

Additional experiments were performed to follow-up on the DTT reduction and gel filtration chromatography done with the PD-10 columns. The goal here was to use a longer column to achieve better resolution of the DTT-treated sample and to process a larger quantity of reduced recA1PI for analysis.

A 1.6 cm inner diameter×90 cm bed height (181 mL column volume) column of Superdex™ 200 prep grade resin was prepared (GE Healthcare Life Sciences). This column was pre-equilibrated with PBS containing 5 mM DTT. A sample of recA1PI in a volume of 9 mL was treated with DTT at a concentration of 50 mM at ambient temperature, overnight. This sample was loaded on the column; the load constituted 5% of the column volume and the column was run at 2 mL/minute (60 cm/h). Constant-volume fractions of 14.5 mL were collected for analysis. Appropriate fractions were pooled and concentrated back to approximately 50 mg/mL using Amicon UltraCel™ 30 kDa MWCO spin concentrators (Millipore). A control sample that was not treated with DTT was also run under identical conditions.

Figure 8:
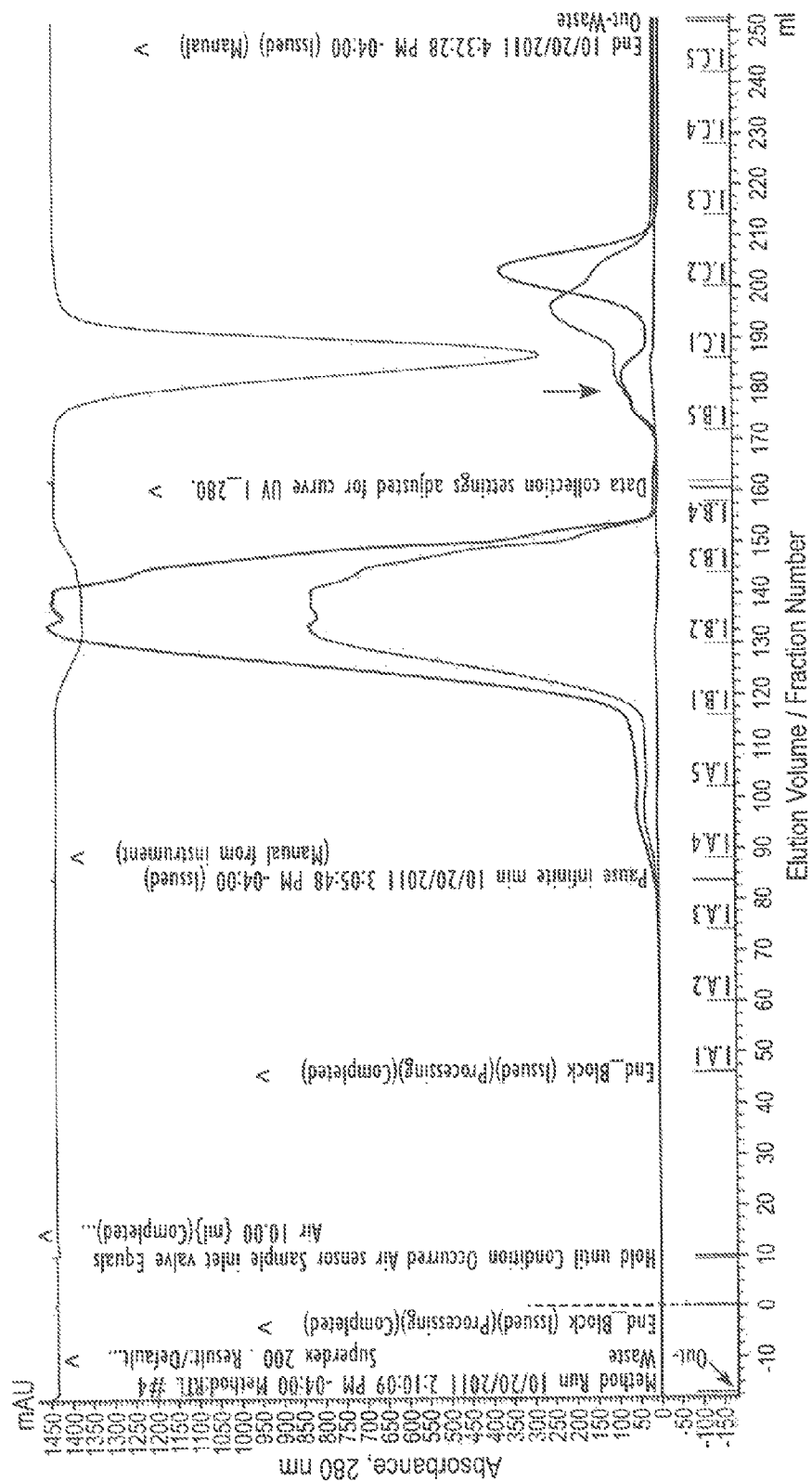
FIG. 8 shows a chromatogram of recA1PI treated with 50 mM DTT and then purified by gel filtration chromatography.
Figure 9:
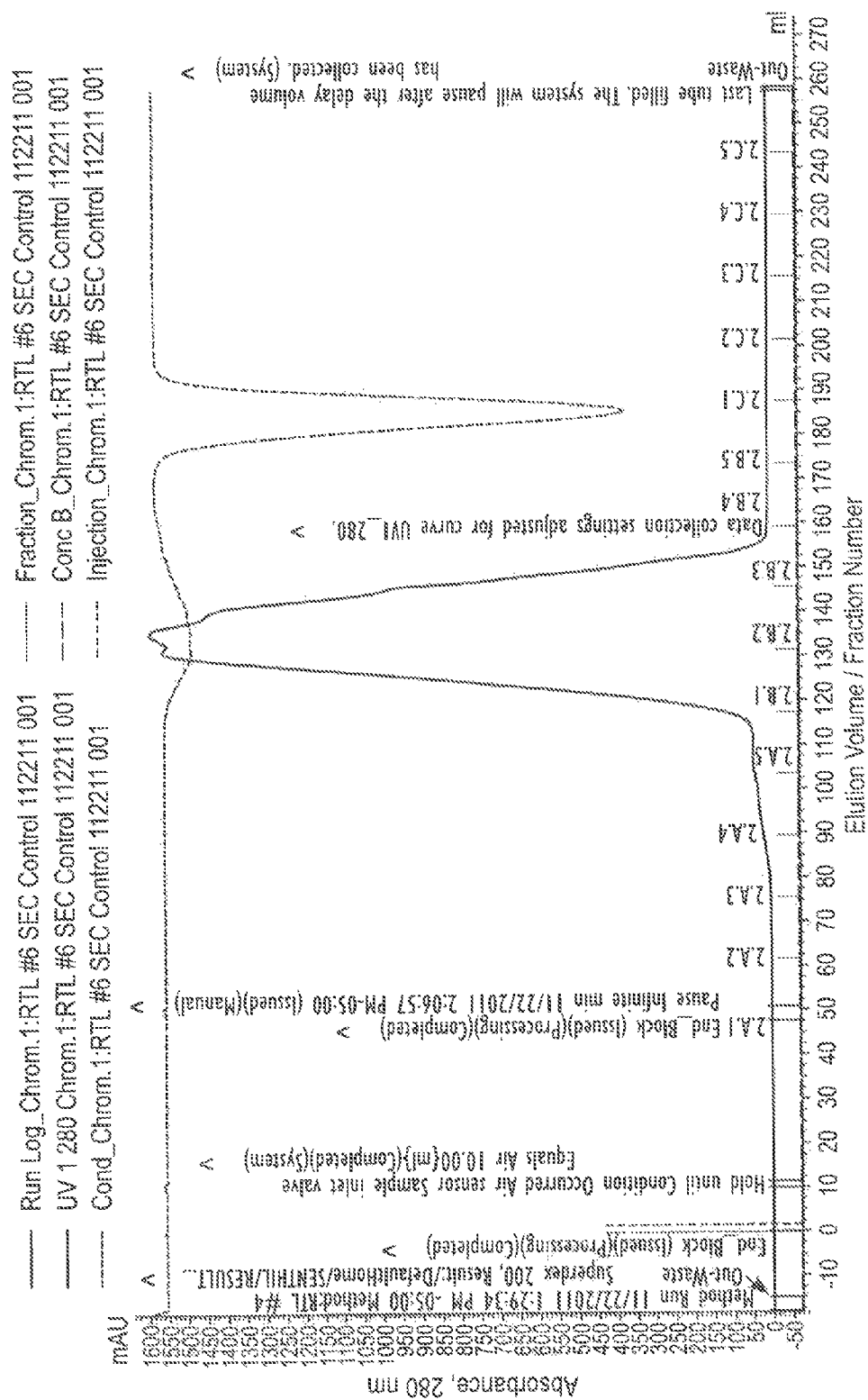
FIG. 9 shows a chromatogram of recA1PI without DTT treatment and then purified by gel filtration chromatography.
Figure 10:
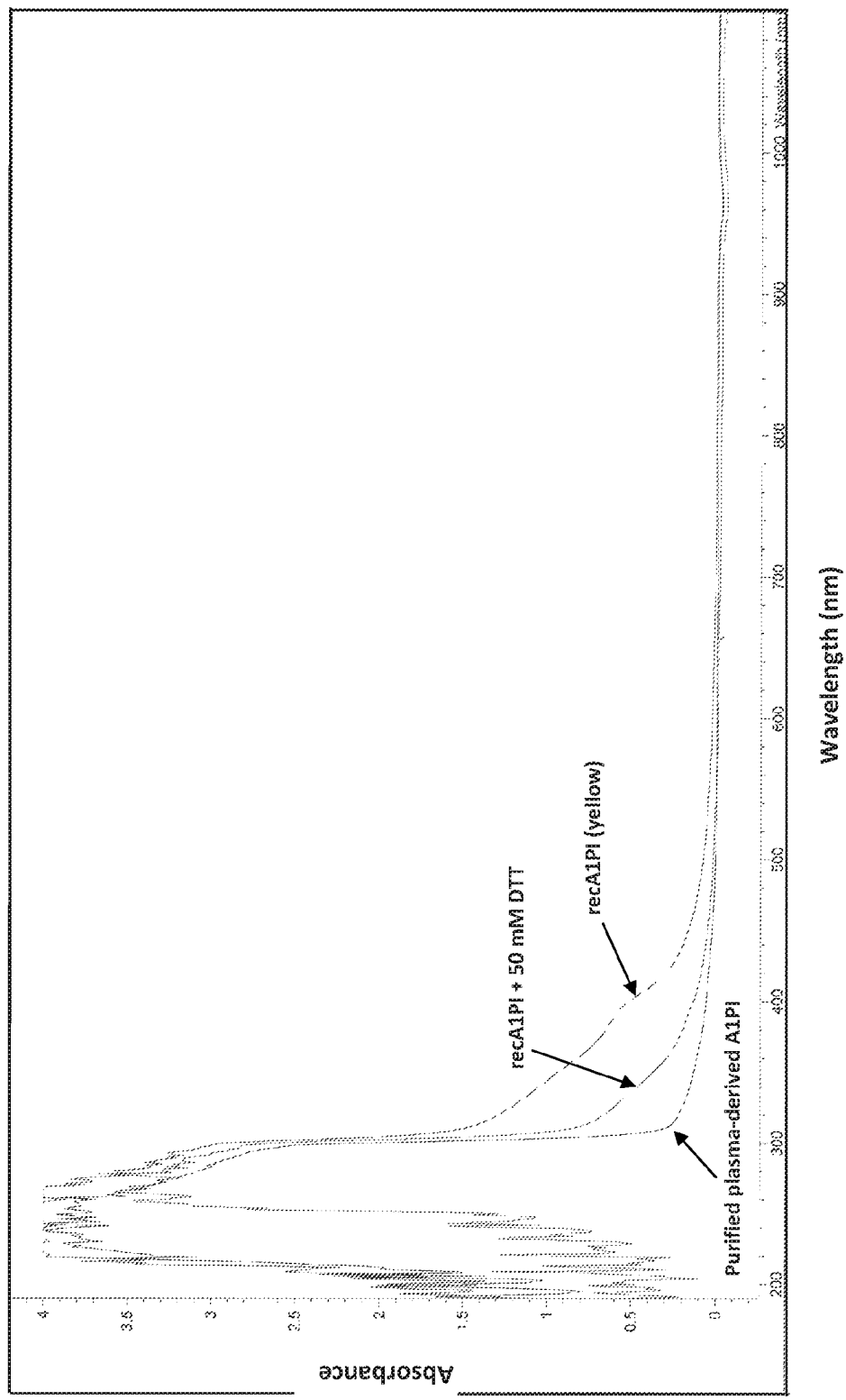
FIG. 10 shows UV-Vis spectra of samples of recA1PI, recA1PI treated with 50 mM DTT, and highly purified, plasma-derived A1PI.

The chromatogram for the 50 mM DTT treated sample is shown in FIG. 8 and the control sample is shown in FIG. 9. There is a distinct smaller, second peak that was seen in the SEC run with the DDT-treated sample. Fractions B1-B3, containing the recA1PI were pooled and concentrated to approximately 50 mg/mL using a 30 kDa MWCO spin concentrator. The concentrated sample was analyzed by UV-Vis spectrophotometry. The UV-Vis spectra shown in FIG. 10, reveals that the characteristic signature of the yellow starting material, recA1PI, is significantly diminished in the concentrate from the reduced, gel filtration eluate. Highly purified, plasma-derived human A1PI was used as a control.

Example 7

DTT Concentration Analysis

The effects of lower concentrations of DTT were analyzed by incubating recA1PI with DTT, purifying the sample using gel filtration chromatography, and then obtaining the UV-Vis spectra of the concentrated purified samples. A 1.6 cm inner diameter×90 cm bed height (181 mL column volume) column of Superdex™ 200 prep grade resin was used (GE Healthcare Life Sciences). This column was pre-equilibrated with PBS containing 5 mM DTT. The recA1PI in a volume of 9 mL was treated with DTT at the appropriate concentration at ambient temperature, overnight. The load constituted 5% of the column volume and the column was run at 2 mL/minute (60 cm/h). Constant volume fractions of 14.5 mL were collected. Appropriate fractions were pooled and concentrated back to approximately 50 mg/mL using 30 kDa MWCO spin concentrators.

Figure 11:
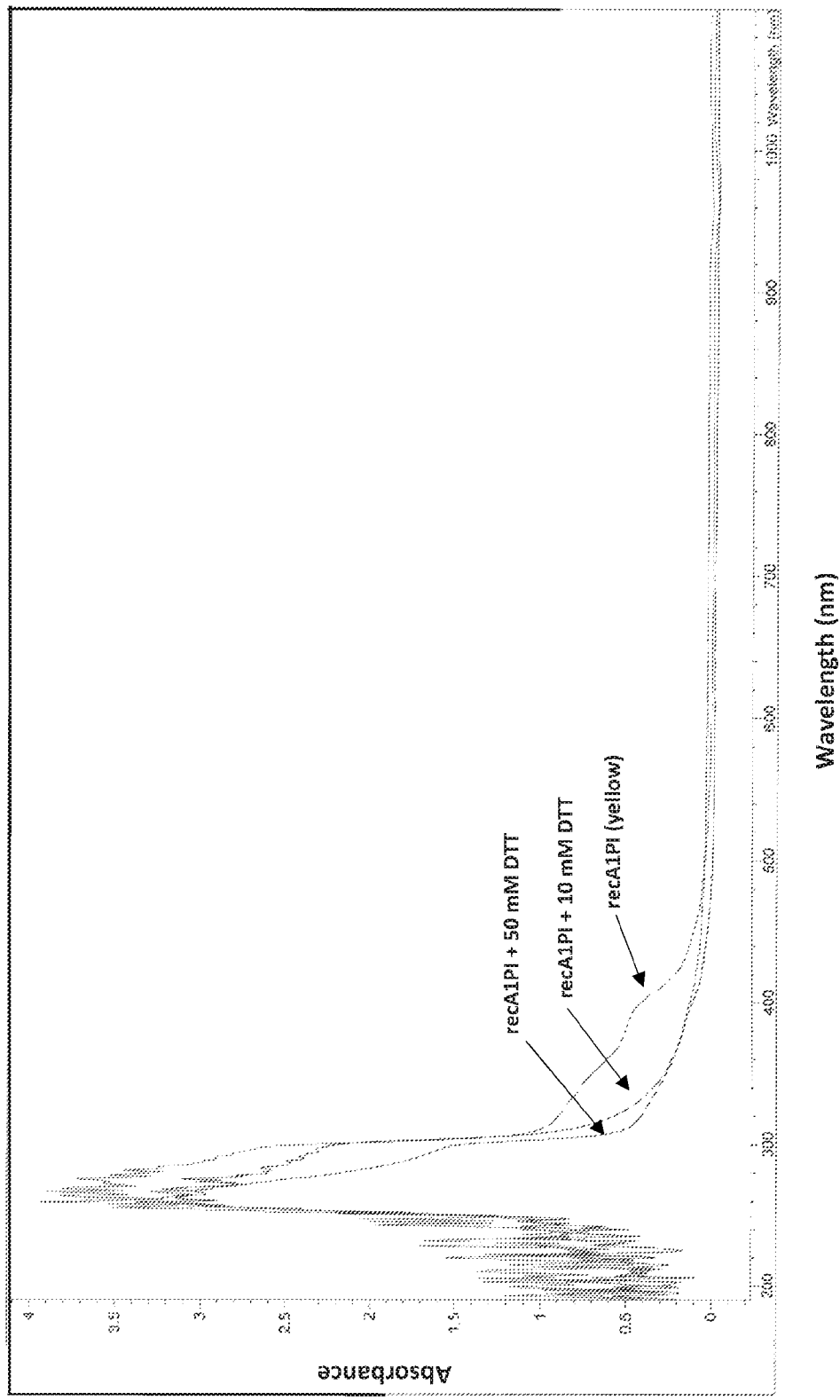
FIG. 11 shows UV-Vis spectra of samples of recA1PI, recA1PI treated with 50 mM DTT, and recA1PI treated with 10 mM DTT.

The UV-Vis spectra of the samples treated with 10 mM DTT and 50 mM DTT shows that the 10 mM DTT concentration is as effective as 50 mM DTT for diminishing the characteristic spectral signature of the yellow colored recA1PI (FIG. 11).

Example 8

Bioanalytical Analysis on DTT-Treated, Gel Filtration-Purified recA1PI

MALDI TOF Analysis

Matrix-assisted laser desorption/ionization time of flight mass spectrometry experiments were performed on recA1PI. The expectation was that the small peaks generated by DTT treatment having a yellow color might contain a species identifiable by mass spectrometry. However, nothing was identified in these samples. Matrix effects may have interfered with the ionization of molecules in the 100-10,000 Da range.

Iron Concentration

Iron ions were suspected as a possible source of the yellow color. Iron is an essential transition metal in cell culture and is added to the upstream cell culture media as ferric ammonium citrate, $Fe_x(NH_4)_yC_6H_5O_7$. Iron analyses showed that a ~30-fold reduction in iron content of the pooled fractions of DTT-reduced recA1PI from the gel filtration column compared to the starting material that had 66 μM of iron. See FIG. 13. The yellow species indicated by the arrow on the chromatogram had ~50% of the iron from the loaded amount.

Activity Analysis

Other than the main peak fractions, none of the smaller peak fractions had recA1PI activity.

Example 9

DTT Gel Filtration Analysis

Figure 12:
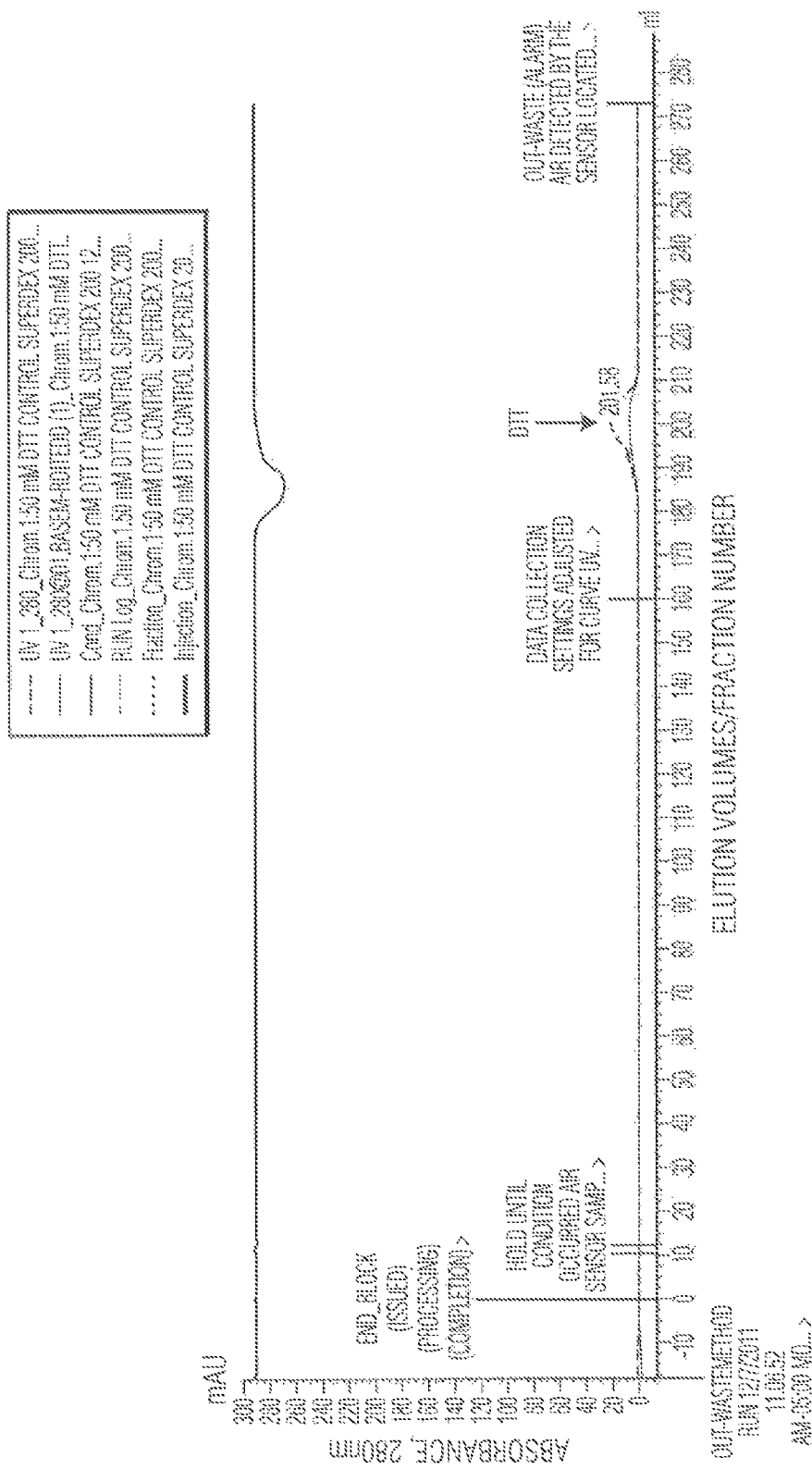
FIG. 12 shows a chromatogram from a gel filtration chromatography run of 50 mM DTT in PBS.
Figure 13:
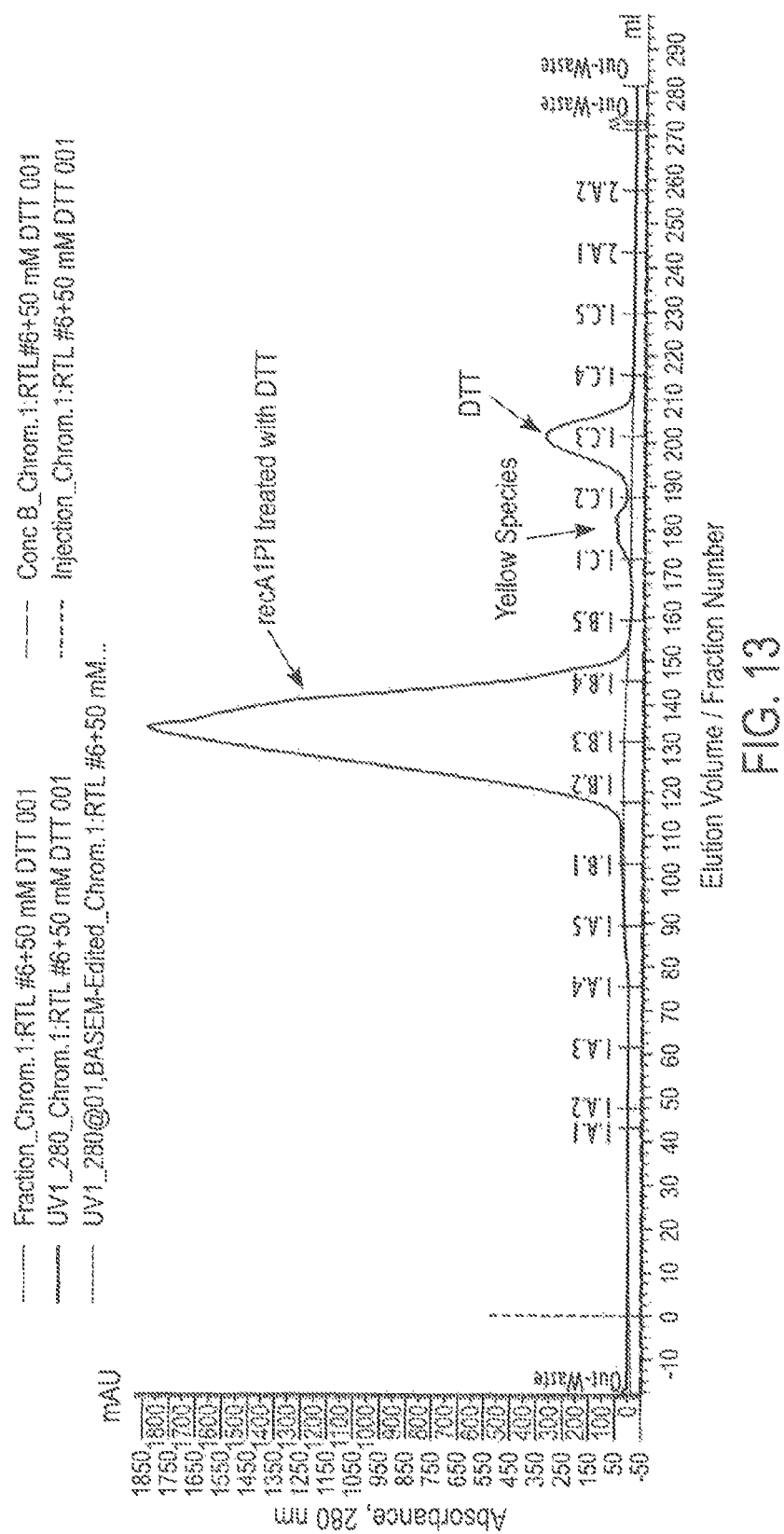
FIG. 13 shows a chromatogram from a gel filtration chromatography run of recA1PI treated with 50 mM DTT in PBS.

A chromatography run was completed with DTT alone in the absence of recA1PI to see the chromatographic profile of DTT in the absence of recA1PI. A single peak was observed with an elution volume of 201 mL (FIG. 12) which corresponds to the last peak, of identical elution volume, seen in the test run with recA1PI sample. The fraction with a slightly yellow color corresponding to the peak indicated by the arrow in FIG. 13 is unique to the DTT-treated recA1PI samples and is absent in the control run with only DTT.

Example 10

Treatment of Purified Plasma-Derived A1PI with 10 mM DTT

Figure 14:
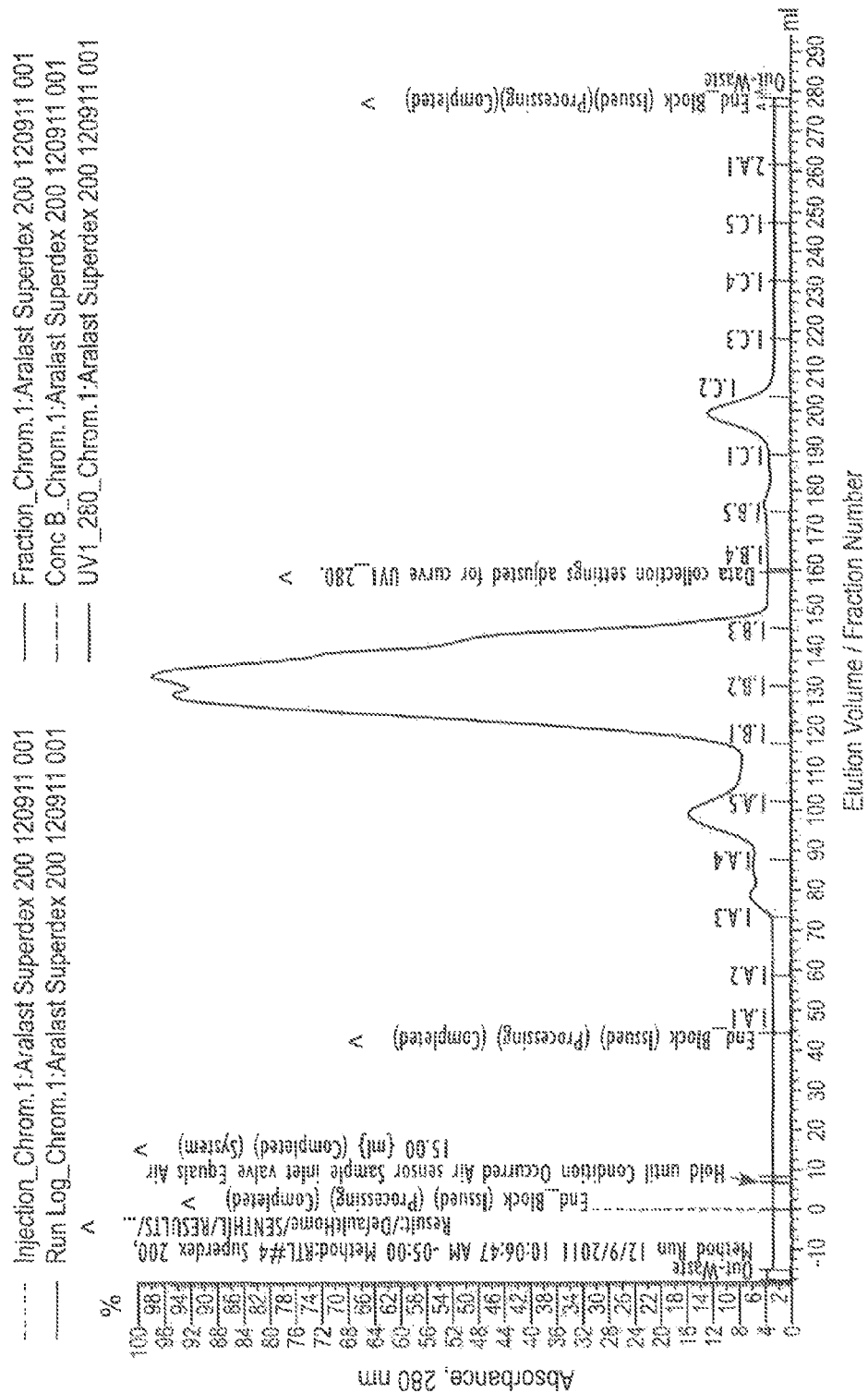
FIG. 14 shows a chromatogram from a gel filtration chromatography run of purified plasma derived A1PI treated with 10 mM DTT.

A plasma-derived A1PI product that has a yellow appearance was tested to determine if treatment with reducing agent would also result in a similar reduction in the yellow color. A 10 mL aliquot of plasma-derived A1PI at approximately 50 mg/mL was treated with DTT at a final concentration of 10 mM. Gel filtration chromatography on Superdex™ 200 prep grade resin was performed as described herein (GE Healthcare Life Sciences). The chromatogram from the run with the DTT-treated plasma-derived A1PI is shown in FIG. 14.

The fractions corresponding to recA1PI under the main peak were pooled and concentrated to 50 mg/mL. The color of the sample was no different from that of the untreated sample. This indicated that the source of yellow color of cell culture-derived recA1PI was different from that of the plasma-derived A1PI.

Example 11

Analysis of Cysteine as a Reducing Agent

Figure 15:
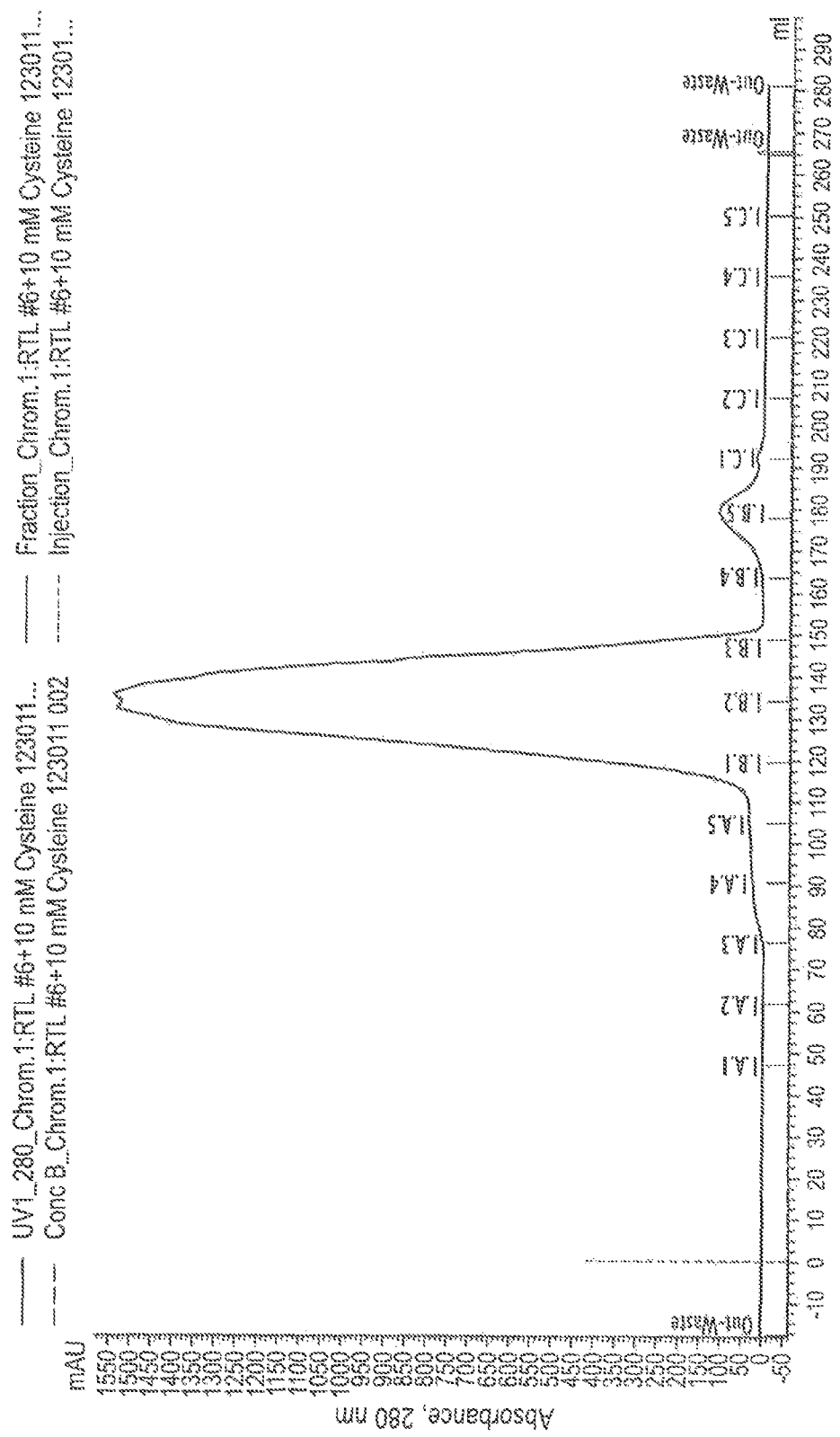
FIG. 15 shows a chromatogram from a gel filtration chromatography column of recA1PI treated with 10 mM cysteine.

Cysteine was examined as an alternative reducing agent because cysteine is inexpensive and readily available. In addition, as an amino acid, cysteine is an acceptable excipient. An experiment was completed where an aliquot of recA1PI was treated with 10 mM cysteine and processed over a gel filtration column. The chromatogram for the run is shown in FIG. 15. The fractions corresponding to recA1PI were pooled and concentrated to 50 mg/mL. Cysteine was also acceptable as reducing agent.

Example 12

Color Analysis

A comparison of the color of samples treated with either DTT or cysteine at 10 mM concentration shows a substantial reduction in yellow color, at comparable protein concentration (~50 mg/mL). The $A_{280}/A_{405}$ ratio was followed as an indicator of yellowness of a sample, the rationale being that the absorbance of a solution at 405 nm is a quantitative measure of yellow color. A higher $A_{280}/A_{405}$ ratio corresponds to a lighter yellow color of the sample. The significant yellow color of the untreated sample is largely removed by the treatment with either DTT or cysteine. However, the yellow color removal was not complete and a tinge of yellow remains in the treated samples. The $A_{280}/A_{405}$ ratio tracks this trend well and a 3-fold reduction is typically seen following treatment with reducing agents. Highly purified plasma-derived A1PI is practically clear with an $A_{208}/A_{405}$ ratio of 428.

Recombinant Cell Culture Derived A1PI Activity Recovery

The recA1PI activity recovery from experiments with size exclusion chromatography and treatment with reducing agents ranged from 80-100% (see Table 1).

TABLE 1

Recombinant cell culture derived A1PI activity recovery from size exclusion chromatography following treatment with DTT or cysteine

| Sample | $A_{280}/A_{405}$ | Activity Recovery |
| --- | --- | --- |
| recA1PI # 4 | 64 | 100% |
| recA1PI # 4 + 50 mM DTT | 281 | 78% |
| recA1PI # 6 | 66 | 100% |
| recA1PI # 6 + 50 mM DTT | 186 | 108%* |
| recA1PI # 6 + 10 mM DTT | 194 | 87% |
| recA1PI # 6 + 10 mM cysteine | 171 | 90% |

*The measured activity of >100% was due to assay-to-assay variability and was interpreted to mean that there was no loss of activity.

Iron Content

The iron concentration of the treated samples was considerably reduced after treatment with reducing agents and chromatographic purification. Reduced and purified samples were analyzed using inductively coupled plasma atomic absorption spectroscopy (ICP-AA). The extent of ion concentration reduction ranged from approximately 14-fold for the cysteine treated sample to 27-fold for the 10 mM DTT-treated sample (Table 2) when compared to the untreated samples.

TABLE 2

Iron concentration of A1PI samples from size exclusion chromatography following treatment with DTT or cysteine

| Sample | Iron Concentration (μM) |
| --- | --- |
| recA1PI # 4 | 66.4 |
| recA1PI # 4 + 50 mM DTT | 3.0 |
| recA1PI # 6 | 12.6 |
| recA1PI # 6 + 10 mM DTT | 0.5 |
| recA1PI # 6 + 10 mM cysteine | 0.8 |

Example 13

Figure 16:
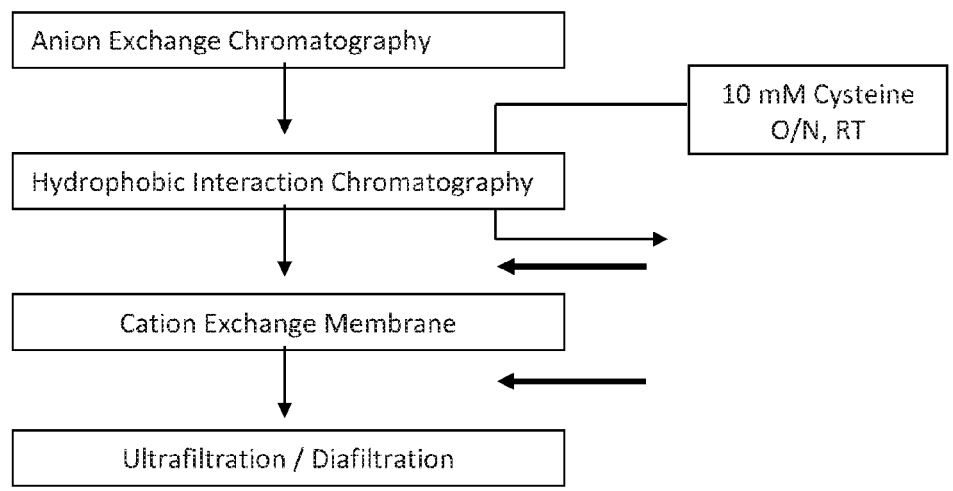
FIG. 16 shows a flow chart of the revised recA1PI purification procedure including a cysteine incubation step. Note that the cysteine incubation can be performed at other steps in the process, such as after hydrophobic interaction chromatography or after passing through the cation exchange membrane (bold arrows).

Revised recA1PI Purification Procedure: Reducing Agent Addition and Incubation Following Anion Exchange Chromatography FIG. 16 shows a flow chart of the revised recA1PI purification procedure, where cysteine is added to the pooled anion exchange eluate. The revised procedure follows. After the solvent/detergent viral inactivation step, cell culture supernatant, having a mass 11.2 kg, was purified on a 5 cm inner diameter×25 cm bed height (500 mL) Capto™ Q column (GE Healthcare Life Sciences) at 300 cm/h. The column was equilibrated in 20 mM $Na_2HPO_4$, pH 6.0; washed with 20 mM $Na_2HPO_4$, 20 mM NaCl, pH 6.0; and eluted with 25 mM $Na_2HPO_4$, 200 mM NaCl, pH 7.0, over 8 CV. The $A_{280}$ of the Q-eluate was 2.4, corresponding to an approximate potency of 2 g/L. A 500 mL aliquot of this Q-eluate containing approximately 1 g of recA1PI by activity was treated with 10 mM cysteine (Acros Chemicals; Thermo Fisher Scientific; New Jersey) and incubated at room temperature overnight (~25° C. ca. 16 h). The treated sample was diluted 42:58 with HIC dilution buffer, 25 mM $Na_2HPO_4$, 100 mM NaCl, 3 M $(NH_4)_2SO_4$, pH 7.0, and used to load an Octyl Sepharose™ column of dimensions, 5 cm inner diameter×10.3 cm bed height (202 ml bed volume). The column was equilibrated with 25 mM $Na_2HPO_4$, 100 mM NaCl, 1.75 M $(NH_4)_2SO_4$, pH 7.0, and eluted with a gradient of 20 mM $Na_2HPO_4$, pH 6.0, over 10 CV. The eluate volume of 620 mL, was concentrated to 50 mL using a LabScale™ TFF system and a Pellicon® 30 kDa, 3×50 cm² filter (Millipore). The sample was further in concentrated to 50 mg/mL using Amicon UltraCel™ 30 kDa MWCO concentrators (Millipore) by centrifugation at 3,500 rpm at 4° C. The concentrated sample was then passed over a Sartobind® S-membrane capsule (Sartorius, Gottingen, Germany) equilibrated in 10 mM sodium citrate buffer, pH 5.4. This sample was diafiltered against 5-column volumes of PBS.

Figure 17:
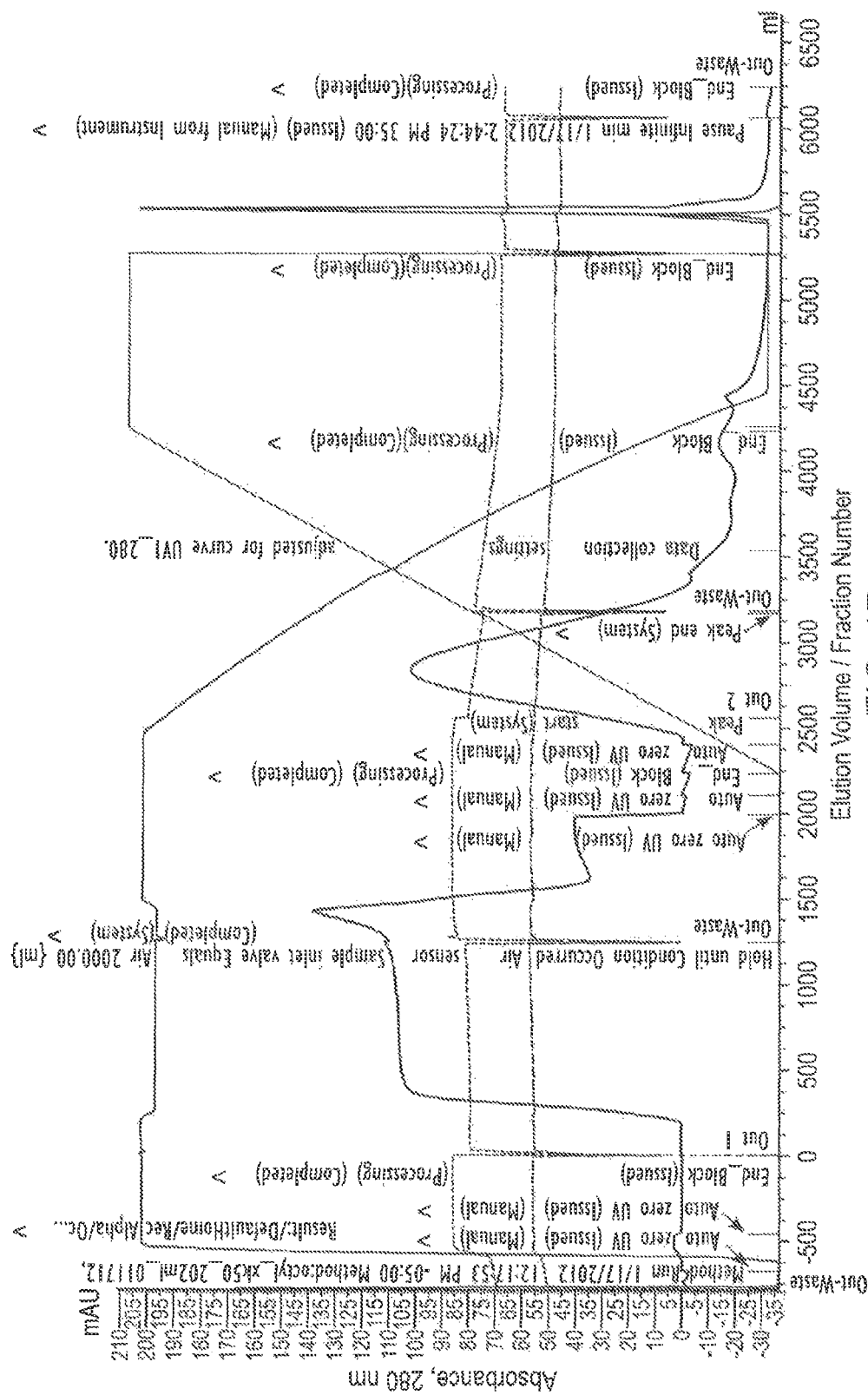
FIG. 17 shows a chromatogram of hydrophobic interaction chromatography on Octyl Sepharose™ with recA1PI not treated with cysteine.
Figure 18:
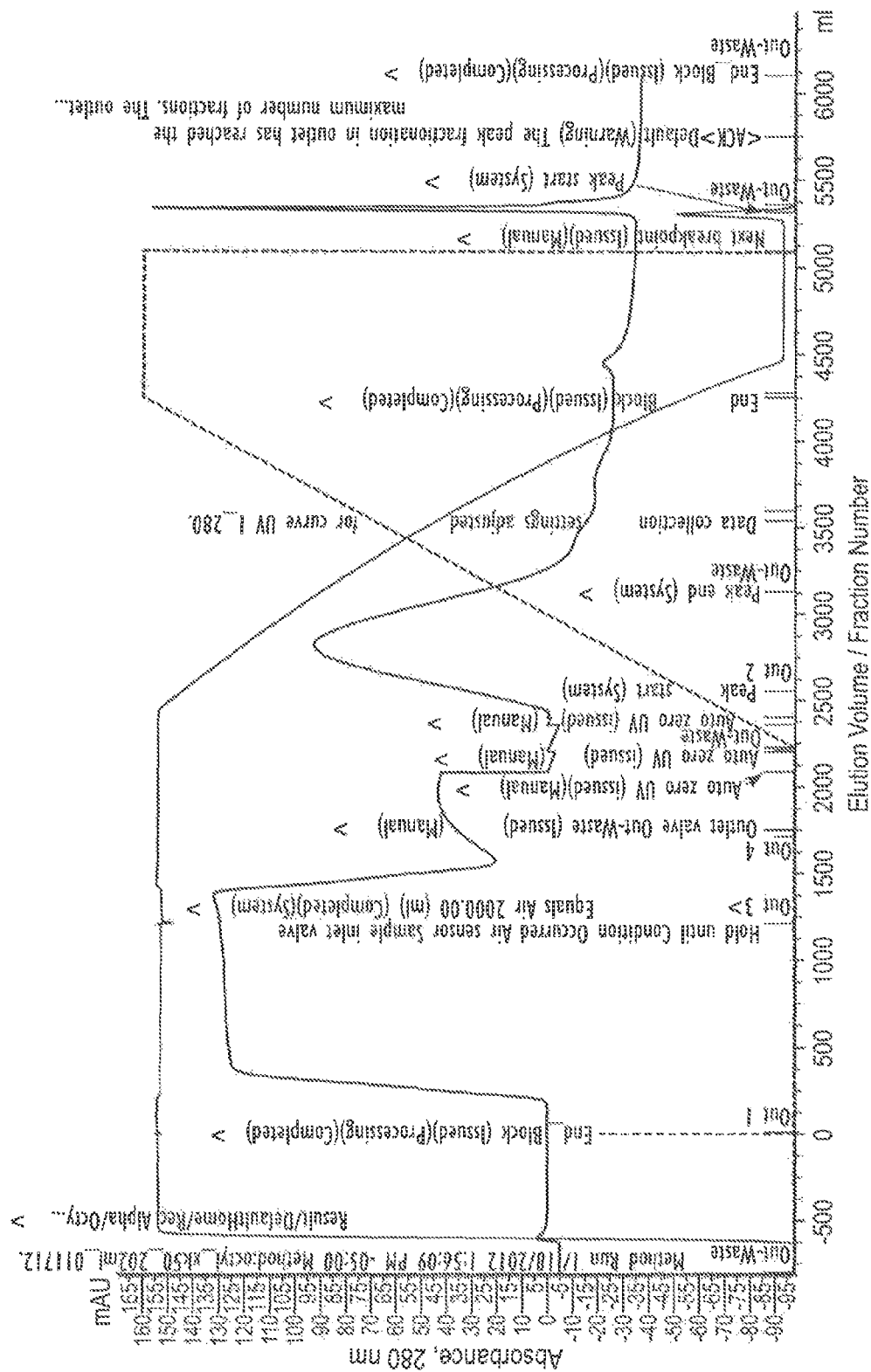
FIG. 18 shows a chromatogram of hydrophobic interaction chromatography on Octyl Sepharose™ with recA1PI following treatment with 10 mM cysteine.
Figure 19:
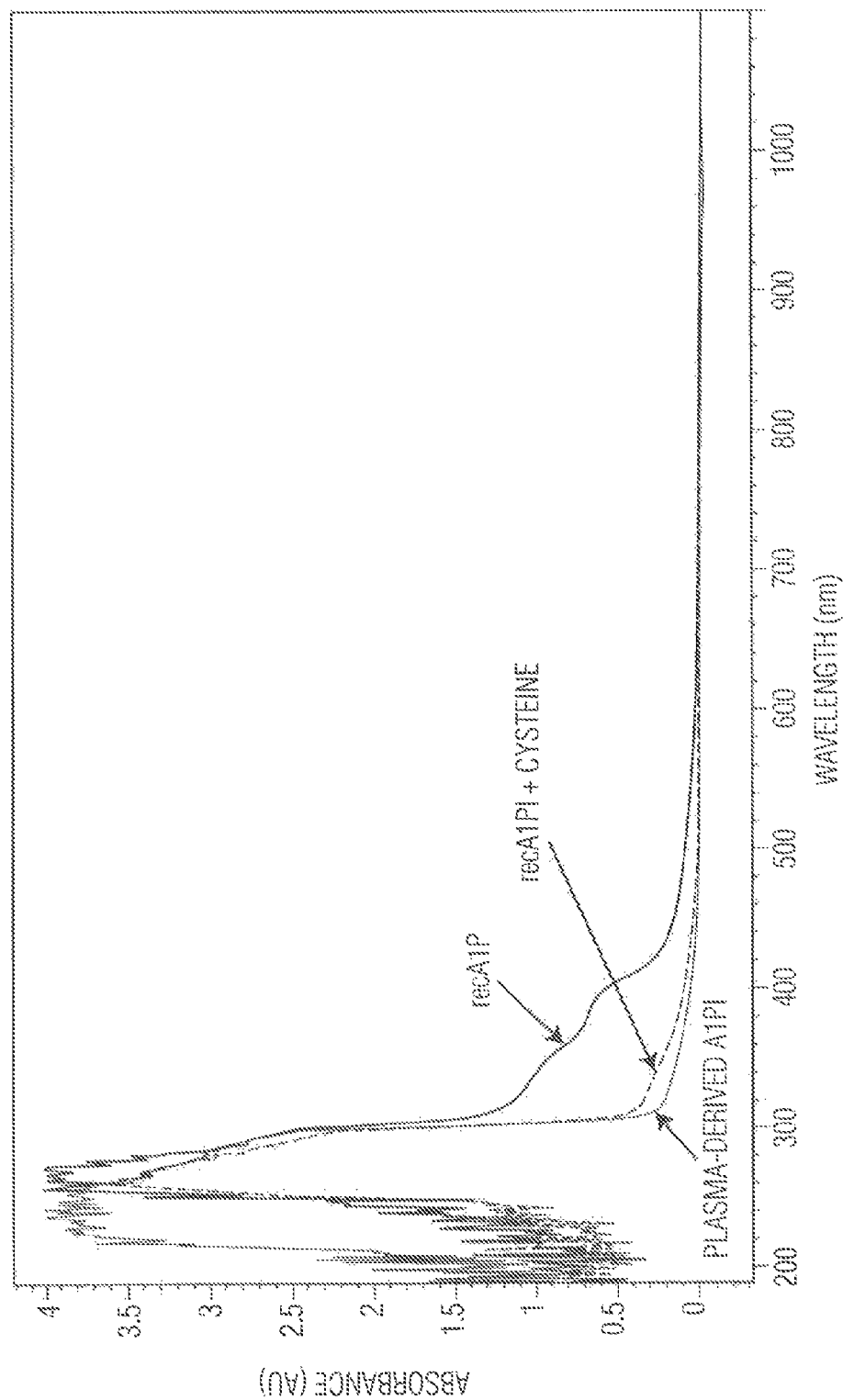
FIG. 19 shows UV-Vis spectra of recA1PI, recA1PI treated with 10 mM cysteine, or highly purified plasma-derived A1PI.

A control run was also performed using an identical volume of Q-eluate and processed over the HIC column in an identical manner, in the absence of cysteine. The HIC chromatography profiles of the control and cysteine-treated test samples were comparable (cf. FIG. 17 and FIG. 18). This indicated that the addition of cysteine did not change the purification profile of recA1PI over the hydrophobic interaction column. When the samples were concentrated to approximately 50 mg/mL, a substantial reduction in the yellow color was observed that corresponded to a 3.4-fold improvement in the $A_{280}/A_{405}$ ratio (i.e., 73 vs. 245). The UV-Vis spectra also reflect this difference, with the profile of the cysteine-treated sample being comparable to that of highly purified plasma-derived API; see FIG. 19.

Accordingly, the overnight cysteine incubation between the anion exchange column and hydrophobic interaction chromatography (see FIG. 16) in preparative-scale runs produces comparable results to those of bench-scale experiments in terms of yellow color clearance and a corresponding improvement in the $A_{280}/A_{405}$ ratio.

The scope of the devices and methods described herein includes all combinations of embodiments, aspects, examples, steps, and preferences herein described.

What is claimed is:

1. A method of purifying cell culture derived human recombinant alpha₁-protease inhibitor (recA1PI) from an aqueous solution comprising recA1PI, comprising:
   (a) performing a viral inactivation step on a solution containing recA1PI;
   (b) passing the virally inactivated solution through an anion exchanger so that recA1PI binds to the anion exchanger;
   (c) eluting recA1PI from the anion exchanger to obtain an anion exchange eluate containing recA1PI;
   (d) adding a reducing agent to the anion exchange eluate containing recA1PI to obtain a reducing solution, wherein the reducing agent is 10 mM cysteine;
   (e) incubating the reducing solution overnight at about room temperature;
   (f) passing the reducing solution through a hydrophobic interaction chromatography (HIC) resin so that recA1PI binds to the HIC resin; and
   (g) eluting recA1PI from the HIC resin to obtain an HIC eluate that contains recA1PI.

2. The method of claim 1, wherein the viral inactivation comprises a solvent/detergent incubation.

3. The method of claim 2, wherein the solvent is added in a range of 0.01% to about 0.5%.

4. The method of claim 2, wherein the detergent is added from about 0.5% to about 2.0% weight per volume of the resulting mixture.

5. The method of claim 2, wherein the solvent/detergent incubation comprises adding about 0.5% polysorbate 20 and about 0.03% tri(n-butyl phosphate) at pH of about 8 and a temperature of about 30° C.

6. The method of claim 1, wherein the anion exchanger is a quaternary ammonium resin.

7. A method of purifying cell culture derived recombinant alpha₁-protease inhibitor (recA1PI) from an aqueous solution comprising recA1PI, comprising:
   (a) performing a viral inactivation step on a solution containing recA1PI;
   (b) passing the virally inactivated solution through an anion exchanger so that recA1PI binds to the anion exchanger;
   (c) eluting recA1PI from the anion exchanger to obtain an anion exchange eluate containing recA1PI;
   (d) adding a reducing agent to the anion exchange eluate containing recA1PI to obtain a reducing solution;
   (e) incubating the reducing solution;
   (f) passing the reducing solution through a hydrophobic interaction chromatography (HIC) resin so that recA1PI binds to the HIC resin; and
   (g) eluting recA1PI from the HIC resin to obtain an HIC eluate that contains recA1PI,
   wherein the reducing agent is 2 mercaptoethanol (2-ME).

8. The method of claim 7, wherein the reducing agent concentration is from about 1 mM to 100 mM.

9. The method of claim 7, wherein the reducing agent concentration is about 10 mM.

10. The method of claim 7, wherein the reducing agent concentration is about 1 mM.

11. The method of claim 7, wherein the reducing incubation step is carried out for about 1 to 24 hours.

12. The method of claim 7, wherein the reducing incubation step is carried out from about 2° C. to 60° C.

13. The method of claim 1, wherein the HIC resin comprises octyl aliphatic groups.

14. The method of claim 1, wherein the method reduces the concentration of iron associated with the recA1PI.

15. The method of claim 14, wherein the iron concentration is reduced (i.e., lowered) 2- to 100-fold.

16. The method of claim 14, wherein the iron concentration is reduced (i.e., lowered) 5- to 50-fold.

17. The method of claim 14, wherein the iron concentration is 10 µM or less in the HIC eluate.

18. The method of claim 14, wherein the iron concentration is 1 µM or less in the HIC eluate.

19. A method of purifying cell culture derived recombinant alpha' proteinase inhibitor (recA1PI) comprising incubating a solution comprising recA1PI with 10 mM cysteine overnight at about room temperature and then separating the recA1PI from the reducing agent.

20. The method of claim 19, wherein the separating the recA1PI from the reducing agent comprises chromatography.

21. The method of claim 20, wherein the chromatography comprises ion exchange, hydrophobic interaction, gel filtration, affinity, immunoaffinity, or combinations thereof.

22. The method of claim 19, wherein the method reduces the concentration of iron associated with the recA1PI.

23. The method of claim 22, wherein the iron concentration is reduced (i.e., lowered) 2- to 100-fold.

24. The method of claim 22, wherein the iron concentration is reduced (i.e., lowered) 5- to 50-fold.

25. The method of claim 22, wherein the iron concentration is 10 µM or less after separating the recA1PI from the reducing agent.

26. The method of claim 22, wherein the iron concentration is 1 µM or less after separating the recA1PI from the reducing agent.

* * * * *

SEQUENCE LISTING

<160> NUMBER OF SEQ ID NOS: 1

<210> SEQ ID NO 1
<211> LENGTH: 418
<212> TYPE: PRT
<213> ORGANISM: Homo sapiens
<220> FEATURE:

```
-continued

<221> NAME/KEY: SIGNAL
<222> LOCATION: (1)..(24)
<220> FEATURE:
<221> NAME/KEY: mat_peptide
<222> LOCATION: (25)..(418)
<220> FEATURE:
<221> NAME/KEY: CARBOHYD
<222> LOCATION: (70)..(70)
<220> FEATURE:
<221> NAME/KEY: CARBOHYD
<222> LOCATION: (107)..(107)
<220> FEATURE:
<221> NAME/KEY: MISC_FEATURE
<222> LOCATION: (256)..(256)
<223> OTHER INFORMATION: C256 S-nitrosylation
<220> FEATURE:
<221> NAME/KEY: CARBOHYD
<222> LOCATION: (271)..(271)
<220> FEATURE:
<221> NAME/KEY: MISC_FEATURE
<222> LOCATION: (376)..(376)
<223> OTHER INFORMATION: proteolytic cleavage site
<220> FEATURE:
<221> NAME/KEY: MISC_FEATURE
<222> LOCATION: (382)..(383)
<223> OTHER INFORMATION: reactive bond

<400> SEQUENCE: 1

Met Pro Ser Ser Val Ser Trp Gly Ile Leu Leu Leu Ala Gly Leu Cys
            -20                 -15                 -10

Cys Leu Val Pro Val Ser Leu Ala Glu Asp Pro Gln Gly Asp Ala Ala
         -5                  -1  1               5

Gln Lys Thr Asp Thr Ser His His Asp Gln Asp His Pro Thr Phe Asn
    10                  15                  20

Lys Ile Thr Pro Asn Leu Ala Glu Phe Ala Phe Ser Leu Tyr Arg Gln
 25                  30                  35                  40

Leu Ala His Gln Ser Asn Ser Thr Asn Ile Phe Phe Ser Pro Val Ser
                45                  50                  55

Ile Ala Thr Ala Phe Ala Met Leu Ser Leu Gly Thr Lys Ala Asp Thr
            60                  65                  70

His Asp Glu Ile Leu Glu Gly Leu Asn Phe Asn Leu Thr Glu Ile Pro
        75                  80                  85

Glu Ala Gln Ile His Glu Gly Phe Gln Glu Leu Leu Arg Thr Leu Asn
    90                  95                 100

Gln Pro Asp Ser Gln Leu Gln Leu Thr Thr Gly Asn Gly Leu Phe Leu
105                 110                 115                 120

Ser Glu Gly Leu Lys Leu Val Asp Lys Phe Leu Glu Asp Val Lys Lys
                125                 130                 135

Leu Tyr His Ser Glu Ala Phe Thr Val Asn Phe Gly Asp Thr Glu Glu
            140                 145                 150

Ala Lys Lys Gln Ile Asn Asp Tyr Val Glu Lys Gly Thr Gln Gly Lys
                155                 160                 165

Ile Val Asp Leu Val Lys Glu Leu Asp Arg Asp Thr Val Phe Ala Leu
            170                 175                 180

Val Asn Tyr Ile Phe Phe Lys Gly Lys Trp Glu Arg Pro Phe Glu Val
185                 190                 195                 200

Lys Asp Thr Glu Glu Glu Asp Phe His Val Asp Gln Val Thr Thr Val
                205                 210                 215

Lys Val Pro Met Met Lys Arg Leu Gly Met Phe Asn Ile Gln His Cys
            220                 225                 230

Lys Lys Leu Ser Ser Trp Val Leu Leu Met Lys Tyr Leu Gly Asn Ala
                235                 240                 245
```

```
Thr Ala Ile Phe Phe Leu Pro Asp Glu Gly Lys Leu Gln His Leu Glu
        250                 255                 260

Asn Glu Leu Thr His Asp Ile Ile Thr Lys Phe Leu Glu Asn Glu Asp
265                 270                 275                 280

Arg Arg Ser Ala Ser Leu His Leu Pro Lys Leu Ser Ile Thr Gly Thr
                285                 290                 295

Tyr Asp Leu Lys Ser Val Leu Gly Gln Leu Gly Ile Thr Lys Val Phe
            300                 305                 310

Ser Asn Gly Ala Asp Leu Ser Gly Val Thr Glu Glu Ala Pro Leu Lys
        315                 320                 325

Leu Ser Lys Ala Val His Lys Ala Val Leu Thr Ile Asp Glu Lys Gly
    330                 335                 340

Thr Glu Ala Ala Gly Ala Met Phe Leu Glu Ala Ile Pro Met Ser Ile
345                 350                 355                 360

Pro Pro Glu Val Lys Phe Asn Lys Pro Phe Val Phe Leu Met Ile Glu
                365                 370                 375

Gln Asn Thr Lys Ser Pro Leu Phe Met Gly Lys Val Val Asn Pro Thr
            380                 385                 390

Gln Lys
```